(12) United States Patent
Okamoto et al.

(10) Patent No.: US 12,372,494 B2
(45) Date of Patent: **\*Jul. 29, 2025**

(54) GAS SENSOR

(71) Applicant: NGK INSULATORS, LTD., Aichi (JP)

(72) Inventors: Taku Okamoto, Nagoya (JP); Soichiro Yoshida, Nagoya (JP); Ryo Hashikawa, Nagoya (JP)

(73) Assignee: NGK INSULATORS, LTD., Nagoya (JP)

( * ) Notice: Subject to any disclaimer, the term of this patent is extended or adjusted under 35 U.S.C. 154(b) by 854 days.

This patent is subject to a terminal disclaimer.

(21) Appl. No.: 17/531,870

(22) Filed: Nov. 22, 2021

(65) Prior Publication Data

US 2022/0178869 A1 Jun. 9, 2022

(30) Foreign Application Priority Data

Dec. 9, 2020 (JP) .................................. 2020-204045
Jun. 22, 2021 (JP) .................................. 2021-103242

(51) Int. Cl.
*G01N 27/406* (2006.01)
*G01N 27/30* (2006.01)
(Continued)

(52) U.S. Cl.
CPC ......... *G01N 27/409* (2013.01); *G01N 27/301* (2013.01); *G01N 27/4065* (2013.01);
(Continued)

(58) Field of Classification Search
CPC ............. G01N 27/4074; G01N 27/301; G01N 27/4067; G01N 27/4076; G01N 27/409;
(Continued)

(56) References Cited

U.S. PATENT DOCUMENTS

2002/0050455 A1 5/2002 Kurokawa et al.
2011/0132775 A1 6/2011 Kawai et al.
(Continued)

FOREIGN PATENT DOCUMENTS

JP    2001281211 A  * 10/2001
JP    2011-137806 A   7/2011
(Continued)

OTHER PUBLICATIONS

U.S. Appl. No. 17/825,062, filed May 26, 2022.
(Continued)

*Primary Examiner* — James Lin
*Assistant Examiner* — Vivian A Tran
(74) *Attorney, Agent, or Firm* — Mattingly & Malur, PC

(57) ABSTRACT

A gas sensor includes a sensor element including an element body, a measurement pump cell being configured to pump out oxygen from surroundings of an inner measurement electrode to surroundings of an outer measurement electrode, and a measurement voltage detection sensor cell that detects a measurement voltage between a reference electrode and the inner measurement electrode, and a pump cell controller that executes a normal time measurement pump control process of pumping out oxygen in the measurement chamber during a normal operation time of the sensor element so that the measurement voltage reaches a normal time target value, and executes a start-up time measurement pump control process of pumping out oxygen in the measurement chamber at a start-up time of the sensor element earlier than the normal operation time so that the measurement voltage reaches a start-up time target value higher than the normal time target value.

7 Claims, 7 Drawing Sheets

(51) Int. Cl.
*G01N 27/407* (2006.01)
*G01N 27/409* (2006.01)
*G01N 27/41* (2006.01)
*G01N 27/419* (2006.01)
*G01N 33/00* (2006.01)

(52) U.S. Cl.
CPC ....... *G01N 27/4067* (2013.01); *G01N 27/407* (2013.01); *G01N 27/41* (2013.01); *G01N 27/419* (2013.01); *G01N 33/0037* (2013.01)

(58) Field of Classification Search
CPC .................. G01N 27/41; G01N 27/419; G01N 27/406–4071; G01N 27/4075; G01N 27/417
See application file for complete search history.

(56) References Cited

U.S. PATENT DOCUMENTS

| | | | |
|---|---|---|---|
| 2016/0258897 A1* | 9/2016 | Sakakibara | G01N 27/41 |
| 2019/0285572 A1 | 9/2019 | Watanabe et al. | |
| 2020/0200700 A1 | 6/2020 | Okamoto et al. | |
| 2020/0264127 A1 | 8/2020 | Shimizu et al. | |
| 2020/0309727 A1 | 10/2020 | Okamoto et al. | |

FOREIGN PATENT DOCUMENTS

| | | | |
|---|---|---|---|
| JP | 2016-166871 A | | 9/2016 |
| JP | 2017181069 A | * | 10/2017 |
| JP | 2019-158816 A | | 9/2019 |
| JP | 2020-101493 A | | 7/2020 |
| JP | 2020-134297 A | | 8/2020 |
| JP | 2020-159881 A | | 10/2020 |

OTHER PUBLICATIONS

U.S. Appl. No. 17/825,080, filed May 26, 2022.
International Search Report and Written Opinion received in corresponding International Application No. PCT/JP2021/035843 dated Dec. 21, 2021.
International Search Report and Written Opinion received in corresponding International Application No. PCT/JP2021/035842 dated Dec. 21, 2021.
International Preliminary Report on Patentability received in corresponding International Application No. PCT/JP2021/035843 dated Jun. 22, 2023.
International Preliminary Report on Patentability received in corresponding International Application No. PCT/JP2021/035842 dated Jun. 22, 2023.
Non-Final Office Action received in corresponding Pending U.S. Appl. No. 17/825,062 dated Nov. 19, 2024.

* cited by examiner

GAS SENSOR

CROSS-REFERENCE TO RELATED APPLICATION

The present application claims priority from Japanese Patent Application No. 2020-204045 filed on Dec. 9, 2020, and Japanese Patent Application No. 2021-103242 filed on Jun. 22, 2021, the entire contents of which are incorporated herein by reference.

BACKGROUND OF THE INVENTION

1. Field of the Invention

The present invention relates to a gas sensor.

2. Description of the Related Art

Hitherto, a gas sensor that detects a specific gas concentration, such as NOx, in a measurement-object gas, such as the exhaust gas of an automobile, is known. For example, PTL 1 describes a gas sensor including a sensor element having a plurality of oxygen-ion-conductive solid electrolyte layers, a measurement electrode disposed inside the sensor element, and a heater disposed inside the sensor element. In this gas sensor, the specific gas concentration in the measurement-object gas is detected based on the pump current which flows when the measurement-object gas is introduced around the measurement electrode and the oxygen around the measurement electrode is pumped out. The heater heats the sensor element up to a temperature at which the solid electrolyte layers are activated, and keeps the temperature.

CITATION LIST

Patent Literature

PTL 1: Japanese Unexamined Patent Application Publication No. 2016-166871

SUMMARY OF THE INVENTION

It takes time for such a gas sensor to be able to correctly detect a specific gas concentration after the heater starts to be energized, and the time taken is called light-off time. The light-off time tends to be longer as it takes more time to pump out oxygen (oxygen not produced from a specific gas) so as to cause essentially no effect on the measurement accuracy, the oxygen being present in a measurement chamber, where the measurement electrode is disposed, since before the use of the sensor element. In recent years, the need to reduce the light-off time in such a gas sensor has increased due to increased regulation of emission control.

The present invention has been devised to solve such a problem, and it is a main object to reduce the light-off time of the sensor element.

The present invention employs the following device to achieve the above-described object.

A gas sensor of the present invention includes: a sensor element including an element body which includes an oxygen-ion-conductive solid electrolyte layer, and is internally provided with a measurement-object gas flow portion that introduces a measurement-object gas and flows the measurement-object gas, a measurement pump cell having an outer measurement electrode provided outside the element body to be in contact with the measurement-object gas, and an inner measurement electrode disposed in a measurement chamber of the measurement-object gas flow portion, the measurement pump cell being configured to pump out oxygen from surroundings of the inner measurement electrode to surroundings of the outer measurement electrode, a reference electrode disposed inside the element body to come into contact with a reference gas which serves as a reference for detection of a specific gas concentration in the measurement-object gas, and a measurement voltage detection sensor cell that detects a measurement voltage between the reference electrode and the inner measurement electrode; a pump cell controller that executes a normal time measurement pump control process of pumping out oxygen in the measurement chamber during a normal operation time of the sensor element by controlling the measurement pump cell so that the measurement voltage reaches a normal time target value, and executes a start-up time measurement pump control process of pumping out oxygen in the measurement chamber at a start-up time of the sensor element earlier than the normal operation time by controlling the measurement pump cell so that the measurement voltage reaches a start-up time target value higher than the normal time target value; and a specific gas concentration detection section that detects the specific gas concentration in the measurement-object gas based on a measurement pump current which flows through the measurement pump cell by the normal time measurement pump control process.

In this gas sensor, during a normal operation time of the sensor element, normal time measurement pump control process is executed to pump out the oxygen in the measurement chamber by controlling the measurement pump cell so that the measurement voltage reaches a normal time target value. Then, the specific gas concentration in the measurement-object gas is detected based on the measurement pump current which flows through the measurement pump cell by the normal time measurement pump control process. Furthermore, in the gas sensor, at a start-up time of the sensor element earlier than the normal operation time, a start-up time measurement pump control process is executed to pump out the oxygen in the measurement chamber by controlling the measurement pump cell so that the measurement voltage reaches a start-up time target value higher than a normal time target value. In other words, in the start-up time measurement pump control process, the oxygen in the measurement chamber is pumped out with the target value for the oxygen concentration in the measurement chamber lower than the target value during the normal operation time. Thus, as compared with when the normal time measurement pump control process is executed since the start-up time of the sensor element, the oxygen which has been present in the measurement chamber since before the start-up of the sensor element can be quickly removed from the measurement chamber. Therefore, the light-off time of the sensor element is reduced. Here, the oxygen which has been present in the measurement chamber since before the start-up of the sensor element includes, for example, the oxygen molecules ($O_2$) present in the space in the measurement chamber, the oxygen molecules ($O_2$) adhering to the surface of an inner measurement electrode, and the oxygen (which oxidizes the constituent material) binding to the constituent material for the inner measurement electrode.

The gas sensor of the present invention may includes: a heater that heats the element body; and a heater controller that executes a heater control process of energizing the heater to cause the heater to generate heat so that a sensor element temperature, which is a temperature of the heater or the element body, reaches a predetermined target temperature. After the heater control process is started, when the sensor element temperature reaches a level higher than or equal to a predetermined threshold lower than or equal to the target temperature, the pump cell controller may start the start-up time measurement pump control process. In this manner, the start timing for the start-up time measurement pump control process can be appropriately determined based on the sensor element temperature. The predetermined threshold may be a value lower than the target temperature. Here, "energizing the heater to cause the heater to generate heat so that a sensor element temperature reaches a predetermined target temperature" includes a case where the heater is controlled based on the sensor element temperature itself, and a case where the heater is controlled based on a value (for example, the resistance value of the heater, the resistance value of an electrical circuit containing the solid electrolyte) convertible to the sensor element temperature. Examples of the resistance value of an electrical circuit containing a solid electrolyte include, for example, the resistance value of the measurement pump cell, and the resistance value of the measurement voltage detection sensor cell.

In the gas sensor of the present invention, the sensor element may have an adjustment pump cell that adjusts an oxygen concentration in an oxygen concentration adjustment chamber provided on an upstream side of the measurement chamber of the measurement-object gas flow portion, and the pump cell controller may execute an adjustment pump control process of operating the adjustment pump cell at the start-up time of the sensor element, and when determining based on the operation of the adjustment pump cell that the oxygen concentration in the oxygen concentration adjustment chamber is stabilized, may make switching from the start-up time measurement pump control process to the normal time measurement pump control process. Here, before the start-up of the sensor element, not only the measurement chamber, but also the oxygen concentration adjustment chamber on the upstream side thereof is in a state (such as an air atmosphere) in which much oxygen (oxygen not produced from a specific gas) is present. At the start-up time of the sensor element, the pump cell controller executes adjustment pump cell control process, thereby making it possible to also remove the oxygen which has been present in the oxygen concentration adjustment chamber since before the start-up of the sensor element. Since the oxygen concentration adjustment chamber and the measurement chamber communicate with each other, the oxygen in the measurement chamber can also be removed by the operation of the adjustment pump cell. Furthermore, as mentioned above, the oxygen concentration adjustment chamber and the measurement chamber communicate with each other, thus when the oxygen concentration in the oxygen concentration adjustment chamber is stabilized, the oxygen in the measurement chamber is also pumped out sufficiently. Thus, when it is determined based on the operation of the adjustment pump cell that the oxygen concentration in the oxygen concentration adjustment chamber is stabilized, the start-up time measurement pump control process is switched to the normal time measurement pump control process, thereby making it possible to appropriately switch from the start-up time measurement pump control process to the normal time measurement pump control process. Here, "when determining that the oxygen concentration in the oxygen concentration adjustment chamber is stabilized, makes switching from the start-up time measurement pump control process to the normal time measurement pump control process" includes a case where when determining that the oxygen concentration in the oxygen concentration adjustment chamber is stabilized, makes switching immediately, and a case where when determining that the oxygen concentration in the oxygen concentration adjustment chamber is stabilized, makes switching after the timing of the determination. Examples of the latter case include a case where when another condition is satisfied in addition to determining that the oxygen concentration in the oxygen concentration adjustment chamber is stabilized, such as a case where after elapse of a predetermined time since determining that the oxygen concentration in the oxygen concentration adjustment chamber is stabilized, switching is made.

In this case, the adjustment pump cell may include an inner adjustment pump electrode disposed in the oxygen concentration adjustment chamber, and an outer adjustment pump electrode disposed in a portion exposed to the measurement-object gas outside the element body.

In the gas sensor including an adjustment pump cell according to an aspect of the present invention, the oxygen concentration adjustment chamber may have a first internal cavity, and a second internal cavity provided on a downstream side of the first internal cavity and on an upstream side of the measurement chamber, the adjustment pump cell may have a main pump cell that adjusts an oxygen concentration in the first internal cavity, and an auxiliary pump cell that adjusts an oxygen concentration in the second internal cavity, the adjustment pump control process may include an auxiliary pump control process of controlling the auxiliary pump cell so that the oxygen concentration in the second cavity reaches a target concentration, and a main pump control process of controlling the main pump cell so that an auxiliary pump current which flows through the auxiliary pump cell by the auxiliary pump control process reaches a target current, and when determining that the auxiliary pump current is stabilized at around the target current, the pump cell controller may make switching from the start-up time measurement pump control process to the normal time measurement pump control process. In other words, when it is determined that the auxiliary pump current is stabilized at around the target current, it may be determined that the oxygen concentration in the oxygen concentration adjustment chamber is stabilized. In this manner, it is possible to appropriately make switching from the start-up time measurement pump control process to the normal time measurement pump control process based on the auxiliary pump current.

In this case, the main pump cell may include an inner main pump electrode disposed in the first internal cavity, and an outer main pump electrode disposed in a portion exposed to the measurement-object gas outside the element body. The auxiliary pump cell may include an inner auxiliary pump electrode disposed in the second internal cavity, and an outer auxiliary pump electrode disposed in a portion exposed to the measurement-object gas outside the element body.

In the gas sensor of the present invention, when an open time measurement voltage reaches a level higher than or equal to a predetermined threshold, the pump cell controller may make switching from the start-up time measurement pump control process to the normal time measurement pump control process, the open time measurement voltage being a measurement voltage in a state in which no control is performed to pass a current through the inner measurement electrode and the reference electrode. The open time measurement voltage has a value that corresponds to the oxygen concentration in the measurement chamber, thus it is possible to appropriately determine whether or not the oxygen in the measurement chamber has been sufficiently pumped out by comparing the open time measurement voltage with the threshold. Thus, it is possible to appropriately make switching from the start-up time measurement pump control process to the normal time measurement pump control process.

In the gas sensor of the present invention, the inner measurement electrode may contain at least one of Pt and Rh. Noble metal such as Pt and Rh may be bound to the oxygen in the measurement chamber to be oxidized, and the oxygen reduces the accuracy of detection of the specific gas concentration, thus at the start-up time of the sensor element, it is necessary to reduce the oxide of the noble metal contained in the inner measurement electrode and pump out the oxygen from the measurement chamber. It takes more time to reduce the oxide of the noble metal and pump out oxygen than to pump out the oxygen molecules in the measurement chamber, thus when oxidized noble metal is present in the measurement chamber, the light-off time is likely to increase. In the gas sensor of the present invention, at the start-up time of the sensor element, the oxidized noble metal can be reduced early by executing the start-up time measurement pump control process rather than the normal time measurement pump control process, thus the light-off time can be shortened. Thus, when the inner measurement electrode contains at least one of Pt and Rh, execution of the start-up time measurement pump control process has a great significance.

In the gas sensor of the present invention, volume C of the inner measurement electrode may be $8 \times 10^{-3}$ mm$^3$ or more and $32 \times 10^{-3}$ mm$^3$ or less, and a difference ΔV between the start-up time target value and the normal time target value may be 120 mV or more and 200 mV or less. Here, when the volume C is greater than or equal to $8 \times 10^{-3}$ mm$^3$, the ability to pump out the oxygen around the measurement electrode by the measurement pump cell is sufficiently high. When the difference ΔV is less than or equal to 200 mV, the value of a voltage applied to the inner measurement electrode at the time of the start-up time measurement pump control process is not too high. For a greater volume C, the difference ΔV needed to sufficiently enhance the effect of shortening the light-off time tends to increase, however, when the volume C is $8 \times 10^{-3}$ mm$^3$ or more and $32 \times 10^{-3}$ mm$^3$ or less, and the difference ΔV is 120 mV or more and 200 mV or less, the effect of shortening the light-off time can be sufficiently enhanced while satisfying the lower limit value of the volume C and the upper limit value of the difference ΔV mentioned above.

DETAILED DESCRIPTION OF THE INVENTION

Figure 1:
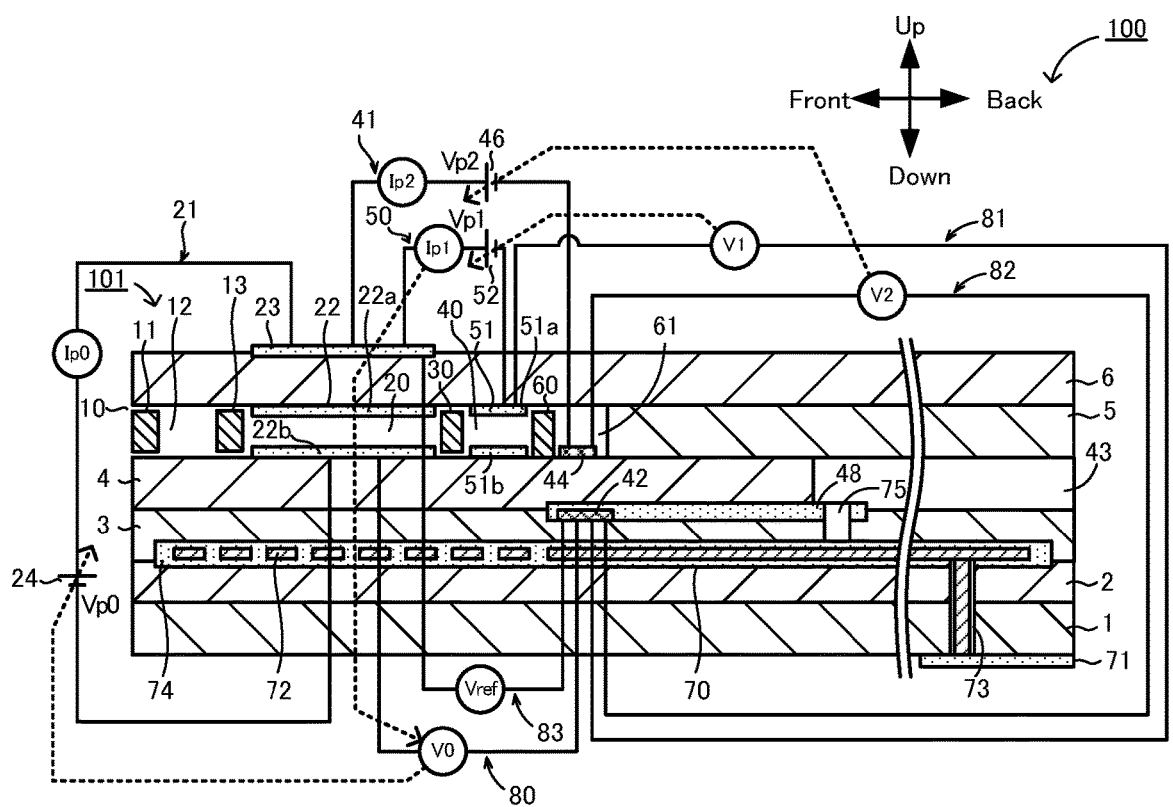
FIG. 1 is a schematic cross-sectional view of a gas sensor 100.
Figure 2:
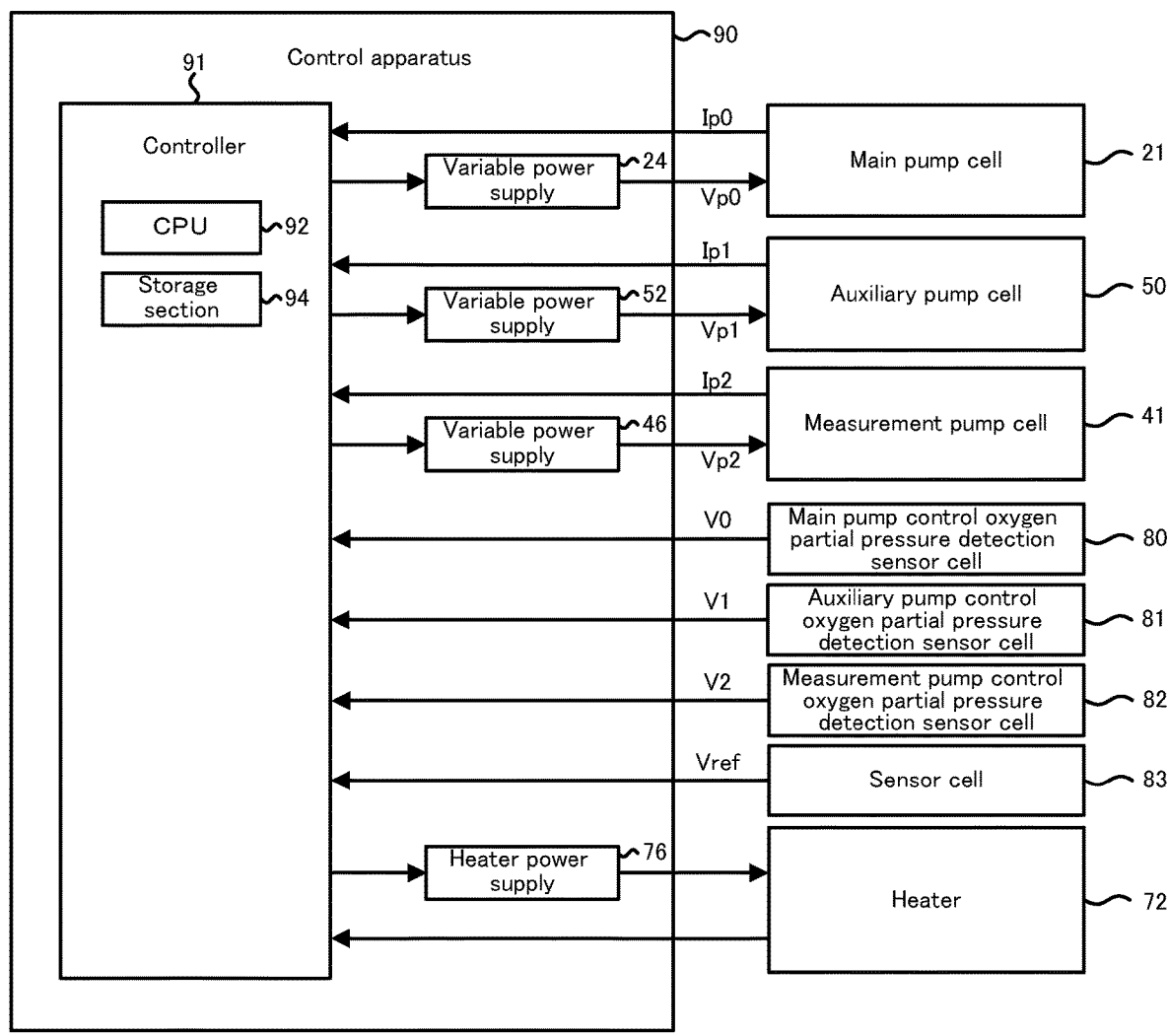
FIG. 2 is a block diagram showing electrical connection relationship between a control apparatus 90, and cells as well as a heater 72.

Next, an embodiment of the present invention will be described using the drawings. FIG. 1 is a schematic cross-sectional view schematically showing an example of a configuration of a gas sensor 100 which is an embodiment of the present invention. FIG. 2 is a block diagram showing electrical connection relationship between a control apparatus 90, and cells as well as a heater 72. The gas sensor 100 is, for example, installed in a pipe, such as an exhaust gas pipe of an internal combustion engine, such as a diesel engine. The gas sensor 100 uses the exhaust gas from the internal combustion engine as a measurement-object gas, and detects the specific gas concentration, such as NOx in the measurement-object gas. The gas sensor 100 includes a long rectangular parallelepiped sensor element 101, cells 15, 21, 41, 50, 80 to 83 each including a part of the sensor element 101, a heater portion 70 provided inside the sensor element 101, and the control apparatus 90 that controls the overall gas sensor 100.

The sensor element 101 is an element having a layered body in which six layers, that is, a first substrate layer 1, a second substrate layer 2, a third substrate layer 3, a first solid electrolyte layer 4, a spacer layer 5, and a second solid electrolyte layer 6, each made up of an oxygen-ion-conductive solid electrolyte layer made of zirconia ($ZrO_2$) or the like, are laminated in this order from a lower side in the drawing. The solid electrolyte forming these six layers is a dense, airtight one. The sensor element 101 is manufactured by, for example, applying predetermined processing, printing of a circuit pattern, and the like on a ceramic green sheet corresponding to each layer, then laminating those sheets, and further firing the sheets to be integrated.

At a tip end portion side of the sensor element 101 (left end portion side in FIG. 1), a gas inlet port 10, a first diffusion controlled portion 11, a buffer space 12, a second diffusion controlled portion 13, a first internal cavity 20, a third diffusion controlled portion 30, a second internal cavity 40, a fourth diffusion controlled portion 60, and a third internal cavity 61 are formed adjacent to each other so as to communicate with each other in this order between the under surface of the second solid electrolyte layer 6 and the top surface of the first solid electrolyte layer 4.

The gas inlet port 10, the buffer space 12, the first internal cavity 20, the second internal cavity 40, and the third internal cavity 61 are spaces of which top parts, bottom parts, and side parts, provided by hollowing the spacer layer 5, are respectively defined by the under surface of the second solid electrolyte layer 6, the top surface of the first solid electrolyte layer 4, and the side surface of the spacer layer 5 inside the sensor element 101.

Each of the first diffusion controlled portion 11, the second diffusion controlled portion 13, and the third diffusion controlled portion 30 is provided as two laterally long slits (openings of which the longitudinal direction is a direction perpendicular to the drawing). The fourth diffusion controlled portion 60 is provided as a single laterally long slit (an opening of which the longitudinal direction is a direction perpendicular to the drawing) formed as a clearance from the under surface of the second solid electrolyte layer 6. A part from the gas inlet port 10 to the third internal cavity 61 is also referred to as measurement-object gas flow portion.

At a location farther from the tip end side than the measurement-object gas flow portion, a reference gas inlet space 43 is provided between the top surface of the third substrate layer 3 and the under surface of the spacer layer 5 at a location at which the side part is defined by the side surface of the first solid electrolyte layer 4. For example, the atmosphere is introduced into the reference gas inlet space 43 as a reference gas at the time of measuring a NOx concentration.

An atmosphere inlet layer 48 is a layer made of porous ceramics. The reference gas is introduced into the atmosphere inlet layer 48 through the reference gas inlet space 43. The atmosphere inlet layer 48 is formed so as to coat the reference electrode 42.

The reference electrode 42 is an electrode formed in such a manner in which the reference electrode 42 is sandwiched by the top surface of the third substrate layer 3 and the first solid electrolyte layer 4. As described above, the atmosphere inlet layer 48 that communicates with the reference gas inlet space 43 is provided around the reference electrode 42. As will be described later, it is possible to measure an oxygen concentration (oxygen partial pressure) in the first internal cavity 20, an oxygen concentration (oxygen partial pressure) in the second internal cavity 40, and an oxygen concentration (oxygen partial pressure) in the third internal cavity 61 by using the reference electrode 42. The reference electrode 42 is formed as a porous cermet electrode (for example, a cermet electrode of Pt and $ZrO_2$).

In the measurement-object gas flow portion, the gas inlet port 10 is a portion that is open to an external space, and a measurement-object gas is taken into the sensor element 101 from the external space through the gas inlet port 10. The first diffusion controlled portion 11 is a portion that applies predetermined diffusion resistance to a measurement-object gas taken in through the gas inlet port 10. The buffer space 12 is a space provided to guide the measurement-object gas introduced from the first diffusion controlled portion 11 to the second diffusion controlled portion 13. The second diffusion controlled portion 13 is a portion that applies predetermined diffusion resistance to the measurement-object gas introduced from the buffer space 12 into the first internal cavity 20. When the measurement-object gas is introduced from the outside of the sensor element 101 into the first internal cavity 20, the measurement-object gas rapidly taken into the sensor element 101 through the gas inlet port 10 due to pressure fluctuations of the measurement-object gas in the external space (due to pulsation of exhaust pressure when the measurement-object gas is the exhaust gas of an automobile) is not directly introduced into the first internal cavity 20 but, after pressure fluctuations of the measurement-object gas are cancelled out through the first diffusion controlled portion 11, the buffer space 12, and the second diffusion controlled portion 13, the measurement-object gas is introduced into the first internal cavity 20. With this configuration, pressure fluctuations of the measurement-object gas introduced into the first internal cavity 20 are almost ignorable. The first internal cavity 20 is provided as a space used to adjust an oxygen partial pressure in the measurement-object gas introduced through the second diffusion controlled portion 13. The oxygen partial pressure is adjusted by the operation of a main pump cell 21.

The main pump cell 21 is an electrochemical pump cell made up of an inner pump electrode 22 having a ceiling electrode portion 22a provided almost all over the under surface of the second solid electrolyte layer 6, facing the first internal cavity 20, the outer pump electrode 23 provided so as to be exposed to the external space in a region of the top surface of the second solid electrolyte layer 6, corresponding to the ceiling electrode portion 22a, and the second solid electrolyte layer 6 sandwiched by these electrodes.

The inner pump electrode 22 is formed over the upper and lower solid electrolyte layers (the second solid electrolyte layer 6 and the first solid electrolyte layer 4) defining the first internal cavity 20, and the spacer layer 5 providing a side wall. Specifically, the ceiling electrode portion 22a is formed on the under surface of the second solid electrolyte layer 6, providing a ceiling surface of the first internal cavity 20, a bottom electrode portion 22b is formed on the top surface of the first solid electrolyte layer 4, providing a bottom surface, a side electrode portion (not shown) is formed on the side wall surface (inner surface) of the spacer layer 5, making both side wall portions of the first internal cavity 20, so as to connect those ceiling electrode portion 22a and the bottom electrode portion 22b, and the inner pump electrode 22 is disposed with a structure in a tunnel form at a portion where the side electrode portion is disposed.

The inner pump electrode 22 and the outer pump electrode 23 each are formed as a porous cermet electrode (for example, a cermet electrode of Pt and $ZrO_2$, having an Au content of 1 percent). The inner pump electrode 22 that contacts with a measurement-object gas is formed by using a material of which the reduction ability for NOx components in the measurement-object gas is lowered.

By passing a pump current Ip0 in a positive direction or a negative direction between the inner pump electrode 22 and the outer pump electrode 23 by applying a desired pump voltage Vp0 between the inner pump electrode 22 and the outer pump electrode 23, the main pump cell 21 is capable of pumping out oxygen in the first internal cavity 20 to the external space or pumping oxygen in the external space into the first internal cavity 20.

In order to detect an oxygen concentration (oxygen partial pressure) in an atmosphere in the first internal cavity 20, an electrochemical sensor cell, that is, a main pump control oxygen partial pressure detection sensor cell 80, is made up of the inner pump electrode 22, the second solid electrolyte layer 6, the spacer layer 5, the first solid electrolyte layer 4, the third substrate layer 3, and the reference electrode 42.

An oxygen concentration (oxygen partial pressure) in the first internal cavity 20 is found by measuring an electromotive force (voltage V0) in the main pump control oxygen partial pressure detection sensor cell 80. In addition, the pump current Ip0 is controlled by executing feedback control over the pump voltage Vp0 of a variable power supply 24 such that the voltage V0 becomes a target value. With this configuration, it is possible to maintain the oxygen concentration in the first internal cavity 20 at a predetermined constant value.

The third diffusion controlled portion 30 is a portion that applies predetermined diffusion resistance to a measurement-object gas of which the oxygen concentration (oxygen partial pressure) is controlled by operation of the main pump cell 21 in the first internal cavity 20 to guide the measurement-object gas to the second internal cavity 40.

The second internal cavity 40 is provided as a space used to further adjust the oxygen partial pressure by using an auxiliary pump cell 50 for the measurement-object gas adjusted in the oxygen concentration (oxygen partial pressure) in the first internal cavity 20 in advance and then introduced through the third diffusion controlled portion 30. With this configuration, it is possible to highly accurately maintain the oxygen concentration in the second internal cavity 40 at a constant value, so it is possible to measure a highly accurate NOx concentration with the gas sensor 100.

The auxiliary pump cell 50 is an auxiliary electrochemical pump cell made up of an auxiliary pump electrode 51 having a ceiling electrode portion 51a provided substantially all over the under surface of the second solid electrolyte layer 6, facing the second internal cavity 40, the outer pump electrode 23 (not limited to the outer pump electrode 23, and an adequate electrode outside the sensor element 101 may be used), and the second solid electrolyte layer 6.

The auxiliary pump electrode 51 is disposed in the second internal cavity 40 with a structure in a similar tunnel form to that of the inner pump electrode 22 provided in the above-described first internal cavity 20. In other words, the auxiliary pump electrode 51 has such a structure in a tunnel form that a ceiling electrode portion 51a is formed on the second solid electrolyte layer 6 providing the ceiling surface of the second internal cavity 40, a bottom electrode portion 51b is formed on the first solid electrolyte layer 4 providing the bottom surface of the second internal cavity 40, a side electrode portion (not shown) that couples those ceiling electrode portion 51a and bottom electrode portion 51b is formed on each of both wall surfaces of the spacer layer 5, providing a side wall of the second internal cavity 40. The auxiliary pump electrode 51, as well as the inner pump electrode 22, is formed by using a material of which the reduction ability for NOx components in the measurement-object gas is lowered.

By applying a desired voltage Vp1 between the auxiliary pump electrode 51 and the outer pump electrode 23, the auxiliary pump cell 50 is capable of pumping out oxygen in an atmosphere in the second internal cavity 40 to the external space or pumping oxygen from the external space into the second internal cavity 40.

In order to control an oxygen partial pressure in an atmosphere in the second internal cavity 40, an electrochemical sensor cell, that is, an auxiliary pump control oxygen partial pressure detection sensor cell 81, is made up of the auxiliary pump electrode 51, the reference electrode 42, the second solid electrolyte layer 6, the spacer layer 5, the first solid electrolyte layer 4, and the third substrate layer 3.

The auxiliary pump cell 50 performs pumping with a variable power supply 52 of which the voltage is controlled in accordance with an electromotive force (voltage V1) detected by the auxiliary pump control oxygen partial pressure detection sensor cell 81. With this configuration, the oxygen partial pressure in an atmosphere in the second internal cavity 40 is controlled to a low partial pressure that substantially does not influence measurement of NOx.

Together with this, its pump current Ip1 is used to control the electromotive force of the main pump control oxygen partial pressure detection sensor cell 80. Specifically, the pump current Ip1 is input to the main pump control oxygen partial pressure detection sensor cell 80 as a control signal, and the gradient of the oxygen partial pressure in the measurement-object gas to be introduced from the third diffusion controlled portion 30 into the second internal cavity 40 is controlled to be constantly unchanged by controlling the above-described target value of the voltage V0. When used as a NOx sensor, the oxygen concentration in the second internal cavity 40 is maintained at a constant value of about 0.001 ppm by the functions of the main pump cell 21 and auxiliary pump cell 50.

The fourth diffusion controlled portion 60 is a portion that applies predetermined diffusion resistance to measurement-object gas of which the oxygen concentration (oxygen partial pressure) is controlled by operation of the auxiliary pump cell 50 in the second internal cavity 40 to guide the measurement-object gas to the third internal cavity 61. The fourth diffusion controlled portion 60 plays a role in limiting the amount of NOx flowing into the third internal cavity 61.

The third internal cavity 61 is provided as a space used to perform a process related to measurement of a nitrogen oxide (NOx) concentration in a measurement-object gas on the measurement-object gas adjusted in oxygen concentration (oxygen partial pressure) in the second internal cavity 40 in advance and then introduced through the fourth diffusion controlled portion 60. Measurement of a NOx concentration is mainly performed by operation of a measurement pump cell 41 in the third internal cavity 61.

The measurement pump cell 41 measures a NOx concentration in the measurement-object gas in the third internal cavity 61. The measurement pump cell 41 is an electrochemical pump cell made up of a measurement electrode 44 provided on the top surface of the first solid electrolyte layer 4, facing the third internal cavity 61, the outer pump electrode 23, the second solid electrolyte layer 6, the spacer layer 5, and the first solid electrolyte layer 4. The measurement electrode 44 is a porous cermet electrode made of a material of which the reduction ability for NOx components in the measurement-object gas is raised as compared to the inner pump electrode 22. The measurement electrode 44 also functions as a NOx reduction catalyst that reduces NOx present in an atmosphere in the third internal cavity 61.

Specifically, the measurement electrode 44 is an electrode containing at least one of Pt and Rh that is a catalytically active noble metal. The measurement electrode 44 is preferably an electrode formed of a cermet containing at least one of Pt and Rh and an oxygen-ion-conductive oxide (here, $ZrO_2$). Furthermore, the measurement electrode 44 is preferably porous body. In this embodiment, the measurement electrode 44 is a porous cermet electrode composed of Pt, Rh, and $ZrO_2$.

The measurement pump cell 41 is capable of pumping out oxygen produced as a result of decomposition of nitrogen oxides in an atmosphere around the measurement electrode 44 and detecting the amount of oxygen produced as a pump current Ip2.

In order to detect an oxygen partial pressure around the measurement electrode 44, an electrochemical sensor cell, that is, a measurement pump control oxygen partial pressure detection sensor cell 82, is made up of the first solid electrolyte layer 4, the third substrate layer 3, the measurement electrode 44, and the reference electrode 42. A variable power supply 46 is controlled in accordance with an electromotive force (voltage V2) detected by the measurement pump control oxygen partial pressure detection sensor cell 82.

A measurement-object gas guided into the second internal cavity 40 reaches the measurement electrode 44 in the third internal cavity 61 through the fourth diffusion controlled portion 60 in a situation in which the oxygen partial pressure is controlled. Nitrogen oxides in the measurement-object gas around the measurement electrode 44 are reduced ($2NO \rightarrow N_2 + O_2$) to produce oxygen. The produced oxygen is to be pumped by the measurement pump cell 41. At this time, the voltage Vp2 of the variable power supply 46 is controlled such that the voltage V2 detected by the measurement pump control oxygen partial pressure detection sensor cell 82 is constant (target value). The amount of oxygen produced around the measurement electrode 44 is proportional to the concentration of nitrogen oxides in the measurement-object gas, so a nitrogen oxide concentration in the measurement-object gas is calculated by using the pump current Ip2 in the measurement pump cell 41.

An electrochemical sensor cell 83 is made up of the second solid electrolyte layer 6, the spacer layer 5, the first solid electrolyte layer 4, the third substrate layer 3, the outer pump electrode 23, and the reference electrode 42, and it is possible to detect an oxygen partial pressure in a measurement-object gas outside the sensor by using an electromotive force (voltage Vref) obtained by the sensor cell 83.

In the gas sensor 100 having such a configuration, a measurement-object gas of which the oxygen partial pressure is maintained at a constantly unchanged low value (a value that substantially does not influence measurement of NOx) is supplied to the measurement pump cell 41 by operating the main pump cell 21 and the auxiliary pump cell 50. Therefore, it is possible to find a NOx concentration in the measurement-object gas in accordance with a pump current Ip2 that flows as a result of pumping out oxygen, produced by reduction of NOx, by the measurement pump cell 41 substantially in proportion to a NOx concentration in the measurement-object gas.

In addition, the sensor element 101 includes the heater portion 70 that plays a role in temperature adjustment for maintaining the temperature of the sensor element 101 by heating in order to increase the oxygen ion conductivity of the solid electrolyte. The heater portion 70 includes a heater connector electrode 71, a heater 72, a through-hole 73, a heater insulating layer 74, and a pressure release hole 75.

The heater connector electrode 71 is an electrode formed in such a manner as to be in contact with the under surface of the first substrate layer 1. Connection of the heater connector electrode 71 to an external power supply allows electric power to be supplied from the outside to the heater portion 70.

The heater 72 is an electric resistor formed in such a manner as to be sandwiched by the second substrate layer 2 and the third substrate layer 3 from upper and lower sides. The heater 72 is connected to the heater connector electrode 71 via the through-hole 73, and is supplied with electric power from a heater power supply 76 (see FIG. 2) to generate heat to increase and retain the temperature of the solid electrolyte forming the sensor element 101.

The heater 72 is embedded all over the region from the first internal cavity 20 to the third internal cavity 61, and is capable of adjusting the overall sensor element 101 to a temperature at which the solid electrolyte is activated.

The heater insulating layer 74 is an electrically insulating layer formed of an insulating material, such as alumina, on the top and under surfaces of the heater 72. The heater insulating layer 74 is formed for the purpose of obtaining an electrical insulation property between the second substrate layer 2 and the heater 72 and an electrical insulation property between the third substrate layer 3 and the heater 72.

The pressure release hole 75 is a portion provided so as to extend through the third substrate layer 3 and the atmosphere inlet layer 48 and communicate with the reference gas inlet space 43. The pressure release hole 75 is formed for the purpose of easing an increase in internal pressure resulting from an increase in temperature in the heater insulating layer 74.

As shown in FIG. 2, the control apparatus 90 includes the above-described variable power supplies 24, 46, 52, the heater power supply 76, and a controller 91. The controller 91 is a microprocessor including a CPU 92, a storage section 94, and the like. The storage section 94 is, for example, a device that stores various programs and various data. The controller 91 receives input of voltage V0 detected by the main pump control oxygen partial pressure detection sensor cell 80, voltage V1 detected by the auxiliary pump control oxygen partial pressure detection sensor cell 81, voltage V2 detected by the measurement pump control oxygen partial pressure detection sensor cell 82, voltage Vref detected by the sensor cell 83, pump current Ip0 detected by the main pump cell 21, pump current Ip1 detected by the auxiliary pump cell 50 and pump current Ip2 detected by the measurement pump cell 41. The controller 91 controls the voltages Vp0, Vp1, Vp2 output by the variable power supplies 24, 46, 52 by outputting a control signal to the variable power supplies 24, 46, 52, thereby controlling the main pump cell 21, the measurement pump cell 41 and the auxiliary pump cell 50. The controller 91 controls the electric power supplied to the heater 72 from the heater power supply 76 by outputting a control signal to the heater power supply 76. The storage section 94 also stores the later-described target values V0*, V1*, V2a*, V2b* and the like. The CPU 92 of the controller 91 controls the cells 21, 41, 50 by referring to these target values V0*, V1*, V2a*, V2b*.

The controller 91 executes an auxiliary pump control process of controlling the auxiliary pump cell 50 so that the oxygen concentration in the second internal cavity 40 reaches a target concentration. Specifically, the controller 91 controls the auxiliary pump cell 50 by executing feedback control on the voltage Vp1 of the variable power supply 52 so that the voltage V1 reaches a constant value (referred to as target value V1*). The target value V1* is defined as the value that causes the oxygen concentration in the second internal cavity 40 to reach a predetermined low oxygen concentration that does not substantially affect measurement of NOx.

The controller 91 executes a main pump control process of controlling the main pump cell 21 so that the pump current Ip1 which flows at the time of adjusting the oxygen concentration in the second internal cavity 40 by the auxiliary pump cell 50 through the auxiliary pump control process reaches a target current (referred to as target value Ip1*). Specifically, the controller 91 makes setting (feedback control) of a target value (referred to as target value V0*) of the voltage V0 based on the pump current Ip1 so that the pump electric current Ip1 flowing by the voltage Vp1 reaches a constant target current Ip1*. The controller 91 then executes feedback control on the pump voltage Vp0 of the variable power supply 24 so that the voltage V0 reaches the target value V0* (in other words, the oxygen concentration in the first internal cavity 20 reaches the target concentration). The gradient of oxygen partial pressure in a measurement-object gas to be introduced from the third diffusion controlled portion 30 into the second internal cavity 40 is made unchanged constantly by the main pump control process. The target value V0* is set to a value which causes the oxygen concentration in the first internal cavity 20 to be higher than 0% and a low oxygen concentration. The pump current Ip0 which flows during the main pump control process varies according to the oxygen concentration in a measurement-object gas (that is, a measurement-object gas in the surroundings of the sensor element 101) flowed into the measurement-object gas flow portion through the gas inlet port 10. Thus, the controller 91 can also detect the oxygen concentration in a measurement-object gas based on the pump current Ip0.

The main pump control process and the auxiliary pump control process described above are also collectively referred as an adjustment pump control process. The first internal cavity 20 and the second internal cavity 40 are also collectively referred as an oxygen concentration adjustment chamber. The main pump cell 21 and the auxiliary pump cell 50 are also collectively referred as an adjustment pump cell. The controller 91 executes the adjustment pump control process, and thereby the adjustment pump cell adjusts the oxygen concentration in the oxygen concentration adjustment chamber.

In addition, the controller 91 executes a measurement pump control process of controlling the measurement pump cell 41 so that the voltage V2 reaches a constant value (target value) (that is, so that the oxygen concentration in the third internal cavity 61 reaches a predetermined low concentration). Specifically, the controller 91 controls the measurement pump cell 41 by executing feedback control on the voltage Vp2 of the variable power supply 46 so that the voltage V2 reaches a target value. Oxygen is pumped out from the third internal cavity 61 by the measurement pump control process. As the measurement pump control process, the controller 91 executes the normal time measurement pump control process to be executed during the normal operation time of the sensor element 101, and the start-up time measurement pump control process to be executed at the start-up time of the sensor element 101 before the normal operation time. The normal time measurement pump control process and the start-up time measurement pump control process have different target values for the voltage V2. A target value of the voltage V2 in the start-up time measurement pump control process is referred to as a start-up time target value V2$a$*. A target value of the voltage V2 in the normal time measurement pump control process is referred to as a normal time target value V2$b$*. The start-up time target value V2$a$* is set to a value higher than the normal time target value V2$b$*. That is, V2$a$* and V2$b$* are set so that V2$a$*>V2$b$*. Here, the voltage V2 is a value associated with the oxygen concentration difference between the surroundings of the reference electrode 42 and the third internal cavity 61. The lower the oxygen concentration in the third internal cavity 61 is, the larger the oxygen concentration difference is, and the voltage V2 also has a higher value. Therefore, the start-up time target value V2$a$* being a value higher than the normal time target value V2$b$* indicates that at the time of execution of the start-up time measurement pump control process, a target value for the oxygen concentration in the third internal cavity 61 is set to a lower value, as compared with the time of execution of the normal time measurement pump control process. In the present embodiment, the normal time target value V2$b$* is set to 400 mV, and the start-up time target value V2$a$* is set to 600 mV.

Execution of the normal time measurement pump control process causes oxygen to be pumped out from the third internal cavity 61 so that the oxygen produced due to reduction of NOx in a measurement-object gas in the third internal cavity 61 become substantially zero. The controller 91 obtains a pump current Ip2 as a detected value according to the oxygen produced in the third internal cavity 61 from a specific gas (here, NOx), and calculates the NOx concentration in a measurement-object gas based on the pump current Ip2.

The storage section 94 stores a relational expression (for example, an expression of a linear function) and a map as a correspondence relation between the pump current Ip2 and the NOx concentration. Such relational expression and map can be determined in advance by an experiment.

Figure 3:
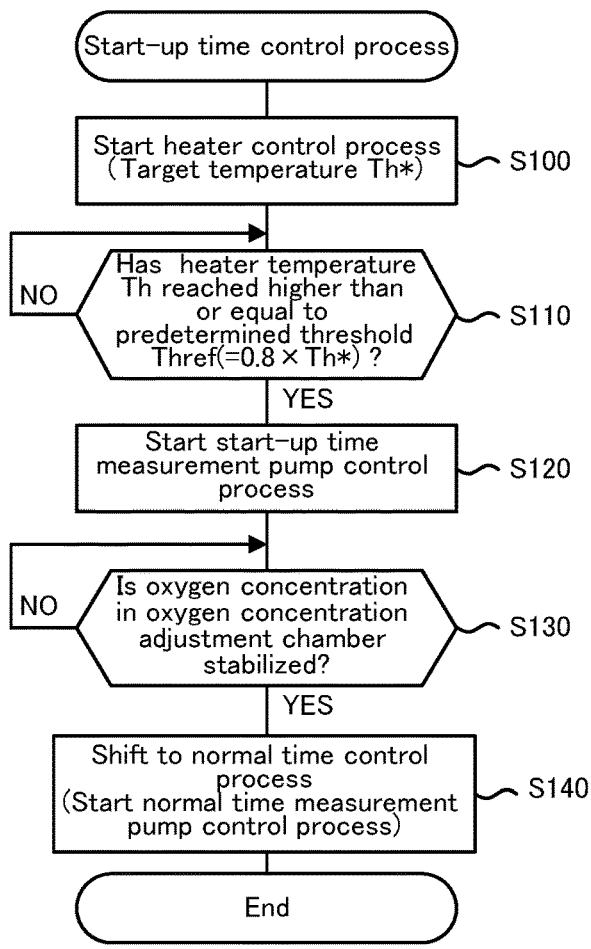
FIG. 3 is a flowchart showing an example of a start-up time control process.
Figure 4:
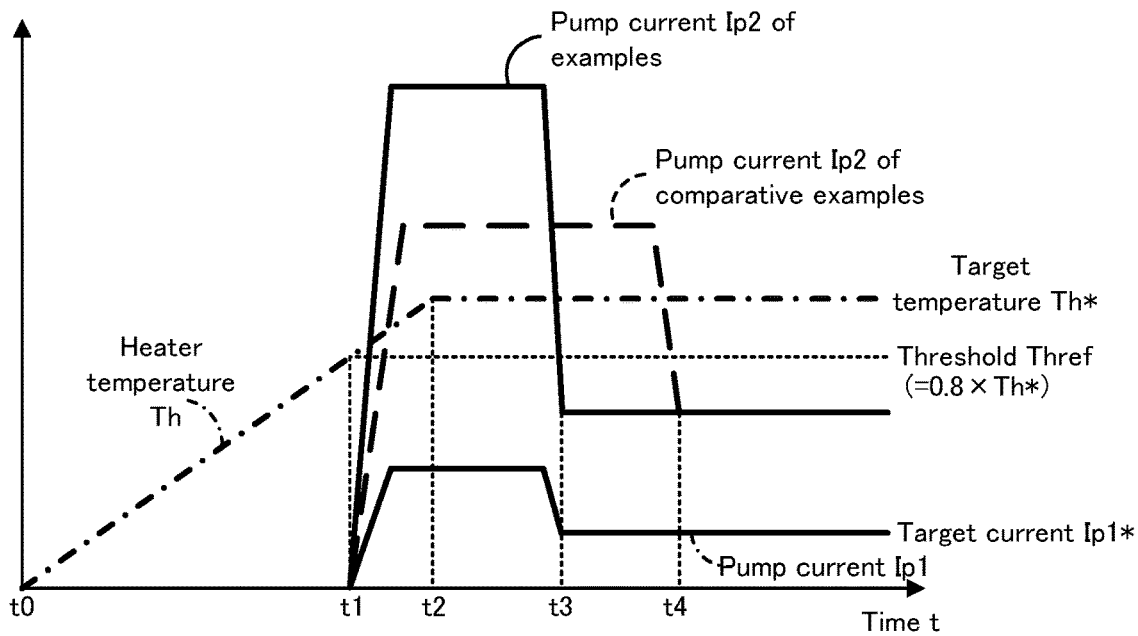
FIG. 4 is a graph showing an example of behavior of a start-up time control process and a normal time control process.

An example of the start-up time control process, which is a process to be executed at the start-up time of the sensor element 101 by the controller 91 of the thus configured gas sensor 100 will be described. FIG. 3 is a flowchart showing an example of the start-up time control process. FIG. 4 is a graph showing an example of the behavior of the start-up time control process and the normal time control process.

When the start-up time control process is started, the CPU 92 of the controller 91 first starts a heater control process of energizing the heater 72 to cause the heater 72 to generate heat so that a heater temperature Th, which is the temperature of the heater 72, reaches a target temperature Th* (step S100). The heater temperature Th can be represented by an expression of a linear function of the resistance value of the heater 72. Thus, in the heater control process of the present embodiment, the CPU 92 calculates the resistance value of the heater 72, and executes feedback control of the heater power supply 76 so that the calculated resistance value reaches a target resistance value (resistance value corresponding to the target temperature Th*). The CPU 92 obtains, for example, the voltage of the heater 72 and the current flowing through the heater 72, and can calculate the resistance value of the heater 72 based on the obtained voltage and current. The CPU 92 may calculate the resistance value of the heater 72, for example, by 3-terminal method or 4-terminal method. The CPU 92 outputs a control signal to the heater power supply 76, and executes feedback control on the electric power supplied by the heater power supply 76 so that the calculated resistance value of the heater 72 reaches a target resistance value. The heater power supply 76 adjusts the electric power supplied to the heater 72, for example, by changing the value of the voltage applied to the heater 72. As shown in FIG. 4, for example, when the heater control process is started at time t0, the heater temperature Th increases to the target temperature Th* as time elapses, and after time t2 at which the heater temperature Th reaches the target temperature Th*, the heater temperature Th is maintained near the target temperature Th*. The target temperature Th* is determined in advance as a temperature (for example, 800° C.) at which the solid electrolyte of the sensor element 101 is sufficiently activated. Note that for the purpose of simplifying the explanation in FIG. 4, the time change of the heater temperature Th is shown by a straight line, but practically, the heater temperature Th may increase curvilinearly, and overshoot may occur in the heater temperature Th before it is stabilized at around the target temperature Th*.

After the heater control process is started in step S100, the CPU 92 determines whether or not a start condition for the start-up time measurement pump control process is satisfied. In the present embodiment, the CPU 92 determines whether or not the heater temperature Th has exceeded a predetermined threshold Thref (step S110), and when a determination result indicates an affirmative determination, the CPU 92 assumes that the start condition for the start-up time measurement pump control process is satisfied. The threshold Thref is a value less than or equal to the target temperature Th*, and may be a value less than the target temperature Th*. The threshold Thref is defined in advance as the lower limit value of the heater temperature Th which is needed to activate (develop ion conductivity of the solid electrolyte) the solid electrolyte (the second solid electrolyte layer 6, the spacer layer 5, and the first solid electrolyte layer 4 in the present embodiment) contained in the measurement pump cell 41 controlled by the start-up time measurement pump control process. For example, the threshold Thref may be defined in advance by an experiment as the lower limit value of the heater temperature Th needed to heat the second solid electrolyte layer 6, the spacer layer 5, and the first solid electrolyte layer 4 up to 600° C. or higher. Alternatively, the threshold Thref may be defined as the value obtained by multiplying the target temperature Th* by a predetermined rate (value less than 1). In the present embodiment, the threshold Thref=0.8×Th*. In other words, the CPU 92 is to determine that the start condition for the start-up time measurement pump control process is satisfied when the heater temperature Th reaches a level higher than or equal to 80% of the target temperature Th*.

When a negative determination is made in step S110, the CPU 92 repeatedly executes step S110 until an affirmative determination is made. When an affirmative determination is made in step S110, the CPU 92 starts the above-described start-up time measurement pump control process (step S120). In the example of FIG. 4, the heater temperature Th reaches the threshold Thref at time t1 before time t2, thus the CPU 92 starts the start-up time measurement pump control process at time t1. When the start-up time measurement pump control process is started, the CPU 92 executes feedback control on the voltage Vp2 of variable power supply 46 so that the voltage V2 reaches the start-up time target value V2a*, thereby controlling the measurement pump cell 41. Application of the voltage Vp2 allows the measurement pump cell 41 to pump out the oxygen present in the third internal cavity 61 to the surroundings of the outer pump electrode 23. At this time, a pump current Ip2 according to the amount of pumped out oxygen flows through the measurement pump cell 41. Here, before the start-up of the sensor element 101, a state (such as an air atmosphere) in which much oxygen (oxygen not produced from a specific gas) is present is achieved in the measurement-object gas flow portion including the third internal cavity 61. Execution of the start-up time measurement pump control process allows such oxygen to be pumped out to the surroundings of the outer pump electrode 23. Thus, as the graph (solid line) of the pump current Ip2 in Example shown in FIG. 4, the pump current Ip2 is rapidly increased from time t1, and a relatively high pump current Ip2 flows. The oxygen which has been present in the third internal cavity 61 since before the start-up of the sensor element 101 specifically includes the oxygen molecules ($O_2$) present in the space in the third internal cavity 61, the oxygen molecules ($O_2$) adhering to the surface of the measurement electrode 44, and the oxygen binding to the constituent material for the measurement electrode 44. In the present embodiment, the measurement electrode 44 contains Rh and Pt, thus at least one of $Rh_2O_3$ and $PtO_2$ may be present in the measurement electrode 44. The oxygen (O) in $Rh_2O_3$ and $PtO_2$ is the oxygen binding to the constituent material for the measurement electrode 44. Not only oxygen molecules, but also the oxygen binding to the constituent material for the measurement electrode 44 can be pumped out by the start-up time measurement pump control process, thus $Rh_2O_3$ and $PtO_2$ are reduced. In the present embodiment, the measurement electrode 44 has a porous body, thus oxygen molecules ($O_2$) may present in the open pores and closed pores of the measurement electrode 44, and these oxygen molecules can also be pumped out by the start-up time measurement pump control process. In the present embodiment, the CPU 92 starts the start-up time measurement pump control process as well as the adjustment pump control process (the main pump control process and the auxiliary pump control process) described above. Consequently, the oxygen which has been present in the oxygen concentration adjustment chamber (the first internal cavity 20 and the second internal cavity 40) since before the start-up of the sensor element 101 is also pumped out to the surroundings of the outer pump electrode 23. Thus, the pump current Ip0 and the pump current Ip1 are rapidly increased from time t1, and relatively high pump current Ip0 and pump current Ip1 flow. Note that illustration of the pump current Ip0 is omitted in FIG. 4. For the convenience of illustration, the pump current Ip1 is shown lower than the pump current Ip2 in FIG. 4; however, the actual magnitude relationship between the pump currents is basically Ip0>Ip1>Ip2.

After the start-up time measurement pump control process is started in step S120, the CPU 92 determines whether or not a termination condition for the start-up time measurement pump control process is satisfied. In the present embodiment, the CPU 92 determines whether or not the oxygen concentration in the oxygen concentration adjustment chamber is stabilized based on the operation of the adjustment pump cell (step S130), and when a determination result indicates an affirmative determination, the CPU 92 assumes that the termination condition for the start-up time measurement pump control process is satisfied. More specifically, when determining that the pump current Ip1 is stabilized at around the target current Ip1*, the CPU 92 determines the oxygen concentration in the oxygen concentration adjustment chamber is stabilized.

For example, as shown in FIG. 4, when the start-up time measurement pump control process, the main pump control process and the auxiliary pump control process are started at time t1, as described above, the pump currents Ip1, Ip2 (and the pump current Ip0) are rapidly increased, and have relatively high values. Thus, as the oxygen in the measurement-object gas flow portion is pumped out, the voltage V2 approaches the start-up time target value V2a*, the voltage V1 approaches the target value V1*, and the pump current Ip1 approaches the target current Ip1*, thus the pump currents Ip1, Ip2 (and the pump current Ip0) are increased once, then gradually decreased. When the oxygen which has been present in the measurement-object gas flow portion since before the start-up of the sensor element 101 is sufficiently pumped out (time t3), thereafter, the voltage V1 is stabilized at substantially the same value as the target value V1*, and the pump current Ip1 is stabilized at substantially the same value as the target current Ip1* (illustration of the voltage V1 is omitted in FIG. 4). Since the second internal cavity 40 and the third internal cavity 61 communicate with each other, not only the oxygen in the second internal cavity 40, but also the oxygen in the third internal cavity 61 can be removed by the operation of the auxiliary pump cell 50. For example, when the oxygen concentration in the second internal cavity 40 is reduced to a level near the target concentration (an oxygen concentration corresponding to the target value V1* of the voltage V1), in the case where the oxygen concentration in the third internal cavity 61 is higher than a target concentration (an oxygen concentration corresponding to the start-up time target value V2a* of the voltage V2), the oxygen in the third internal cavity 61 may be diffused backward (flowed backward) to the second internal cavity 40, and the oxygen can be pumped out by the auxiliary pump cell 50. Thus, when the oxygen concentration in the oxygen concentration adjustment chamber (the first internal cavity 20 and the second internal cavity 40) is stabilized, in other words, when the pump current Ip1 is stabilized at around the target current Ip1*, the oxygen which has been present in the third internal cavity 61 since before the start-up of the sensor element 101 has been sufficiently pumped out. Therefore, it is possible to determine whether or not the oxygen which has been present in the third internal cavity 61 since before the start-up of the sensor element 101 has been sufficiently pumped out based on whether or not the pump current Ip1 is stabilized at around the target current Ip1*. In the determination in step S130, when the pump current Ip1 is once increased and decreased to a level less than or equal to a predetermined threshold, the CPU 92 may determine that the pump current Ip1 is stabilized at around the target current Ip1*. The predetermined threshold in this case is a value which allows to determine that the pump current Ip1 is reduced to a level near the target current Ip1*. The value can be defined in advance as a value greater than or equal to the target current Ip1*, such as the value same as the target current Ip1* or the value greater than the target current Ip1* by 5%. Alternatively, when a state in which the pump current Ip1 has a value in a predetermined range continues for a predetermined time or longer, the CPU 92 may determine that the pump current Ip1 is stabilized at around the target current Ip1*. The predetermined range in this case is a range which allows to determine that the pump current Ip1 is a value around the target current Ip1*, and which can be defined in advance as the range within ±5% of the target current Ip1*, for example. In the present embodiment, when the pump current Ip1 is once increased and decreased to a level less than or equal to the target current Ip1* (at time t3 in FIG. 4), the CPU 92 determines that the pump current Ip1 is stabilized at around the target current Ip1*.

When a negative determination is made in step S130, the CPU 92 repeatedly executes step S130 until an affirmative determination is made. When an affirmative determination is made in step S130, the CPU 92 terminates the above-described start-up time measurement pump control process, and starts the normal time measurement pump control process (step S140) to terminate the start-up time control process. Thus, the process executed by the CPU 92 is shifted from the start-up time control process to the normal time control process. In the normal time control process, the CPU 92 executes the normal time measurement pump control process as well as the above-described adjustment pump control process (the main pump control process and the auxiliary pump control process) continuously from the start-up time control process. The CPU 92 then calculates the NOx concentration in a measurement-object gas based on the pump current Ip2 which flows by the normal time measurement pump control process. In the example of FIG. 4, the pump current Ip1 is not stabilized until time t3, thus the CPU 92 makes a negative determination in step S130, and at time t3, the CPU 92 determines that the pump current Ip1 is stabilized, and makes an affirmative determination in step S130. Thus, the CPU 92 starts the normal time control process from time t3.

As shown in FIG. 4, during execution of the start-up time measurement pump control process (time t1 to t3), the oxygen which has been present in the third internal cavity 61 since before the start-up of the sensor element 101 is being pumped out, thus the pump current Ip2 reaches a high value, and the value of the pump current Ip2 does not reflect a value corresponding to the NOx concentration in a measurement-object gas. After time t3 when pumping out of oxygen is sufficiently performed by the start-up time measurement pump control process, substantially all oxygen present in the third internal cavity 61 is produced from the NOx in a measurement-object gas, thus the value of the pump current Ip2 corresponds to the NOx concentration in a measurement-object gas. For this reason, after time t3, the NOx concentration in a measurement-object gas is detectable based on the pump current Ip2. Thus, the light-off time is the time (t0 to t3) from the start-up time of the sensor element 101 to the time at which the value of the pump current Ip2 reflects the NOx concentration in a measurement-object gas. Note that in order to facilitate understanding of the behavior of the pump current Ip2, FIG. 4 shows the manner in which the NOx concentration in a measurement-object gas is constant, and after time t3, the pump current Ip2 is constant. When the sensor element 101 is actually used, the NOx concentration in a measurement-object gas varies every moment, thus after time t3, the value of the pump current Ip2 varies according to the NOx concentration. Therefore, it is difficult to determine whether or not the sensor element 101 is lighted off based on the value of the pump current Ip2. Thus, in the present embodiment, as described above, the CPU 92 determines whether or not the termination condition for the start-up time measurement pump control process is satisfied based on the value of the pump current Ip1 rather than the pump current Ip2.

Here, in the present embodiment, at the start-up time of the sensor element 101, as described above, the start-up time measurement pump control process of pumping out the oxygen in the third internal cavity 61 by controlling the measurement pump cell 41 so that the voltage V2 reaches the start-up time target value V2a* higher than the normal time target value V2b* is executed. That is, in the start-up time measurement pump control process, the oxygen in the third internal cavity 61 is pumped out with a target value for the oxygen concentration in the third internal cavity 61 set lower than the value during the normal operation time. Thus, as compared with when the normal time measurement pump control process is executed since the start-up time of the sensor element 101, the oxygen which has been present in the third internal cavity 61 since before the start-up can be quickly removed from the third internal cavity 61. For example, the graph (dotted line) of the pump current Ip2 in the comparative example illustrated in FIG. 4 shows the time change of the pump current Ip2 when the adjustment pump control process (the main pump control process and the auxiliary pump control process) is executed from time t1 as well as the normal time measurement pump control process rather than the start-up time measurement pump control process is executed from time t1. In this case, the measurement pump cell 41 is controlled so that the voltage V2 reaches the normal time target value V2b* lower than the start-up time target value V2a*, thus as compared with the graph (solid line) of the pump current Ip2 in Example, the pump current Ip2 has a smaller value, and less amount of oxygen in the third internal cavity 61 is pumped out. Thus, the oxygen in the third internal cavity 61 is sufficiently pumped out at time t4 later than time t3. In other words, the light-off time is longer in the comparative example than in Example. In this manner, in the present embodiment, when the sensor element 101 is started, the start-up time measurement pump control process rather than the normal time measurement pump control process is executed, thus the light-off time of the sensor element 101 can be reduced. Note that although illustration is omitted, when the normal time measurement pump control process and the adjustment pump control process (the main pump control process and the auxiliary pump control process) are executed from time t1, the time until the pump current Ip1 is stabilized at around the target current Ip1* is also time t4 later than time t3.

Note that in FIG. 4, the time at which the pump current Ip2 becomes constant (the time at which the sensor element 101 is lighted off), and the time at which the pump current Ip1 is stabilized at around the target current Ip1* are the same time t3. However, practically, in some cases, the time at which the pump current Ip1 is stabilized at around the target current Ip1* is slightly earlier than time t3. As described above, the auxiliary pump cell 50 can also pump out the oxygen which has flowed backward from the third internal cavity 61 to the second internal cavity 40. However, the auxiliary pump cell 50 cannot pump out the oxygen binding to the constituent material for the measurement electrode 44 and the oxygen molecules present in the closed pores of the measurement electrode 44 because these oxygen do not flow backward. Thus, after the pump current Ip1 is stabilized at around the target current Ip1*, these oxygen which cannot be pumped out by the auxiliary pump cell 50 may be pumped out by the measurement pump cell 41, and the sensor element 101 may be lighted off for the first time. In this case, the CPU 92 preferably continues to execute the start-up time measurement pump control process without executing step S140 during the time until the sensor element 101 is lighted off since the pump current Ip1 is stabilized at around the target current Ip1*. For example, after a predetermined time has elapsed since the CPU 92 makes an affirmative determination in step S130, the CPU 92 may execute step S140. Alternatively, when the CPU 92 makes an affirmative determination in step S130 after a state in which the pump current Ip1 has a value in a predetermined range continues for a predetermined time or longer, the predetermined time may be set to a time nearly equal to the time until the sensor element 101 is lighted off since the pump current Ip1 is stabilized at around the target current Ip1*.

Here, the correspondence relation between the components of the present embodiment and the components of the present invention are made apparent. The layered body in which the six layers, that is, the first substrate layer 1, the second substrate layer 2, the third substrate layer 3, the first solid electrolyte layer 4, the spacer layer 5, and the second solid electrolyte layer 6 of the present embodiment, are laminated in this order corresponds to an element body of the present invention, the outer pump electrode 23 corresponds to an outer measurement electrode, the third internal cavity 61 corresponds to a measurement chamber, the measurement electrode 44 corresponds to an inner measurement electrode, the measurement pump cell 41 corresponds to a measurement pump cell, the reference electrode 42 corresponds to a reference electrode, the measurement pump control oxygen partial pressure detection sensor cell 82 corresponds to a measurement voltage detection sensor cell, the sensor element 101 corresponds to a sensor element, the pump current Ip2 corresponds to a measurement pump current, and the control apparatus 90 corresponds to a pump cell controller and a specific gas concentration detection section. The control apparatus 90 corresponds to a heater controller, the first internal cavity 20 and the second internal cavity 40 correspond to an oxygen concentration adjustment chamber, the inner pump electrode 22 and the auxiliary pump electrode 51 correspond to an inner adjustment pump electrode, the outer pump electrode 23 corresponds to an outer adjustment pump electrode, the main pump cell 21 and the auxiliary pump cell 50 correspond to an adjustment pump cell, and the main pump control process and the auxiliary pump control process correspond to an adjustment pump control process. The inner pump electrode 22 corresponds to an inner main pump electrode, the outer pump electrode 23 corresponds to an outer main pump electrode, the auxiliary pump electrode 51 corresponds to an inner auxiliary pump electrode, the outer pump electrode 23 corresponds to an outer auxiliary pump electrode, and the pump current Ip1 corresponds to an auxiliary pump current.

In the gas sensor 100 of the present embodiment described above in detail, when the sensor element 101 is started, the start-up time measurement pump control process of pumping out the oxygen in the third internal cavity 61 is executed by controlling the measurement pump cell 41 so that the voltage V2 reaches the start-up time target value V2a* higher than the normal time target value V2b*, thus as compared with the case when the normal time measurement pump control process is executed since the start-up time of the sensor element 101, the oxygen which has been present in the third internal cavity 61 since before the start-up can be quickly removed. Therefore, the light-off time of the sensor element 101 is reduced.

After the heater control process is started, the CPU 92 starts the start-up time measurement pump control process when the heater temperature Th reaches a level higher than or equal to the predetermined threshold Thref which is lower than or equal to the target temperature Th*. Therefore, the CPU 92 can appropriately determine the start timing for the start-up time measurement pump control process based on the heater temperature Th.

In addition, the sensor element 101 has an adjustment pump cell that adjusts the oxygen concentration in the oxygen concentration adjustment chamber which is provided on the upstream side of the third internal cavity 61 of the measurement-object gas flow portion. At the start-up time of the sensor element 101, the CPU 92 executes the adjustment pump control process of operating the adjustment pump cell, and when determining based on the operation of the adjustment pump cell that the oxygen concentration in the oxygen concentration adjustment chamber is stabilized, the CPU 92 makes switching from the start-up time measurement pump control process to the normal time measurement pump control process. Here, before the start-up of the sensor element 101, not only the third internal cavity 61, but also the oxygen concentration adjustment chamber on the upstream side thereof assumes a state (such as an air atmosphere) in which much oxygen (oxygen not produced from a specific gas) is present. At the start-up time of the sensor element 101, the CPU 92 executes adjustment pump cell control process, thereby making it possible to also remove the oxygen which has been present in the oxygen concentration adjustment chamber since before the start-up of the sensor element 101. Since the oxygen concentration adjustment chamber and the third internal cavity 61 communicate with each other, the oxygen in the third internal cavity 61 can also be removed by the operation of the adjustment pump cell. In addition, since the oxygen concentration adjustment chamber and the third internal cavity 61 communicate with each other as mentioned above, when the oxygen concentration in the oxygen concentration adjustment chamber is stabilized, the oxygen in the third internal cavity 61 is also pumped out sufficiently. Thus, when it is determined based on the operation of the adjustment pump cell that the oxygen concentration in the oxygen concentration adjustment chamber is stabilized, the start-up time measurement pump control process is switched to the normal time measurement pump control process, thereby making it possible to appropriately switch from the start-up time measurement pump control process to the normal time measurement pump control process.

The oxygen concentration adjustment chamber has the first internal cavity 20, and the second internal cavity 40 provided on the downstream side of the first internal cavity 20 and on the upstream side of the third internal cavity 61, and the adjustment pump cell has the main pump cell 21 that adjusts the oxygen concentration in the first internal cavity 20, and the auxiliary pump cell 50 that adjusts the oxygen concentration in the second internal cavity 40. The adjustment pump control process includes: the auxiliary pump control process of controlling the auxiliary pump cell 50 so that the oxygen concentration in the second internal cavity 40 reaches a target concentration; and the main pump control process of controlling the main pump cell 21 so that the pump current Ip1 flows through the auxiliary pump cell 50 by the auxiliary pump control process reaches the target current Ip1*. When determining that the pump current Ip1 is stabilized at around the target current Ip1*, the CPU 92 makes switching from the start-up time measurement pump control process to the normal time measurement pump control process. Thus, it is possible to appropriately make switching from the start-up time measurement pump control process to the normal time measurement pump control process based on the pump current Ip1.

The measurement electrode 44 contains at least one of Pt and Rh. Noble metal such as Pt and Rh may be bound to the oxygen in the third internal cavity 61 to be oxidized, and the oxygen reduces the accuracy of detection of the specific gas concentration, thus at the start-up time of the sensor element 101, it is necessary to reduce the oxide of the noble metal contained in the measurement electrode 44, and pump out the oxygen from the third internal cavity 61. It takes more time to reduce the oxide of the noble metal and pump out oxygen than to pump out the oxygen molecules in the third internal cavity 61, thus when oxidized noble metal is present in the third internal cavity 61, the light-off time is likely to increase. In the gas sensor 100 of the present embodiment, at the start-up time of the sensor element 101, execution of the start-up time measurement pump control process rather than the normal time measurement pump control process enables the oxidized noble metal to be reduced early, thus the light-off time can be shortened. Thus, in the present embodiment in which the measurement electrode 44 contains Pt and Rh, execution of the start-up time measurement pump control process has a great significance.

Note that the present invention is not limited to the above-described embodiment, and may be, of course, implemented in various modes within the technical scope of the present invention.

For example, in the above-described embodiment, when determining that the pump current Ip1 is stabilized at around the target current Ip1*, the CPU 92 determines that the termination condition for the start-up time measurement pump control process is satisfied, and makes switching from the start-up time measurement pump control process to the normal time measurement pump control process; however, the configuration is not limited thereto. The termination condition for the start-up time measurement pump control process may be defined so that the start-up time measurement pump control process can be terminated when the sensor element 101 is lighted off, in other words, when the oxygen in the third internal cavity 61 is sufficiently pumped out. The start-up time measurement pump control process may be terminated, for example, when a predetermined time has elapsed since the heater 72 is initially energized, or when a predetermined time has elapsed since the start-up time measurement pump control process is started.

Figure 5:
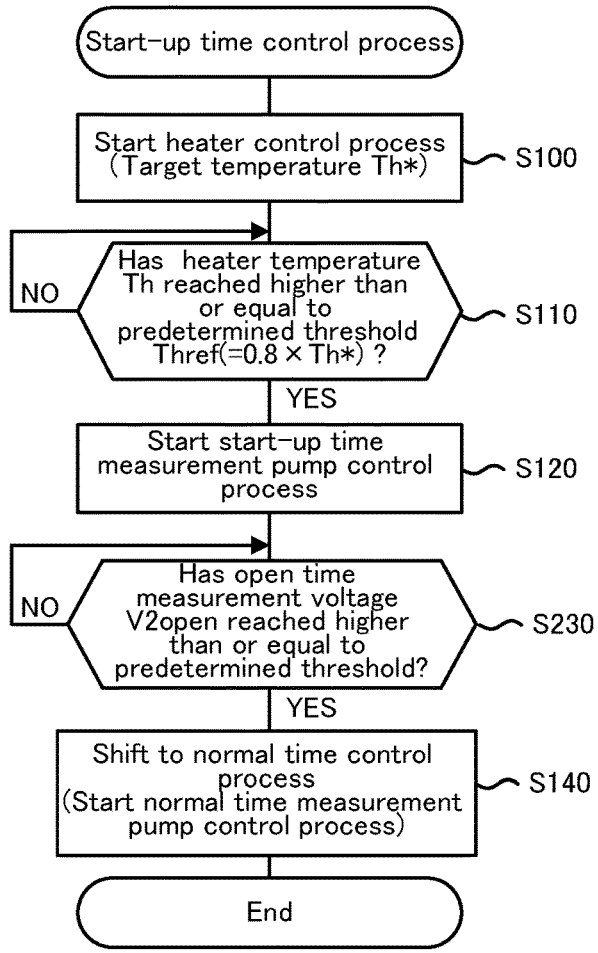
FIG. 5 is a flowchart showing an example of a start-up time control process of a modification.
Figure 6:
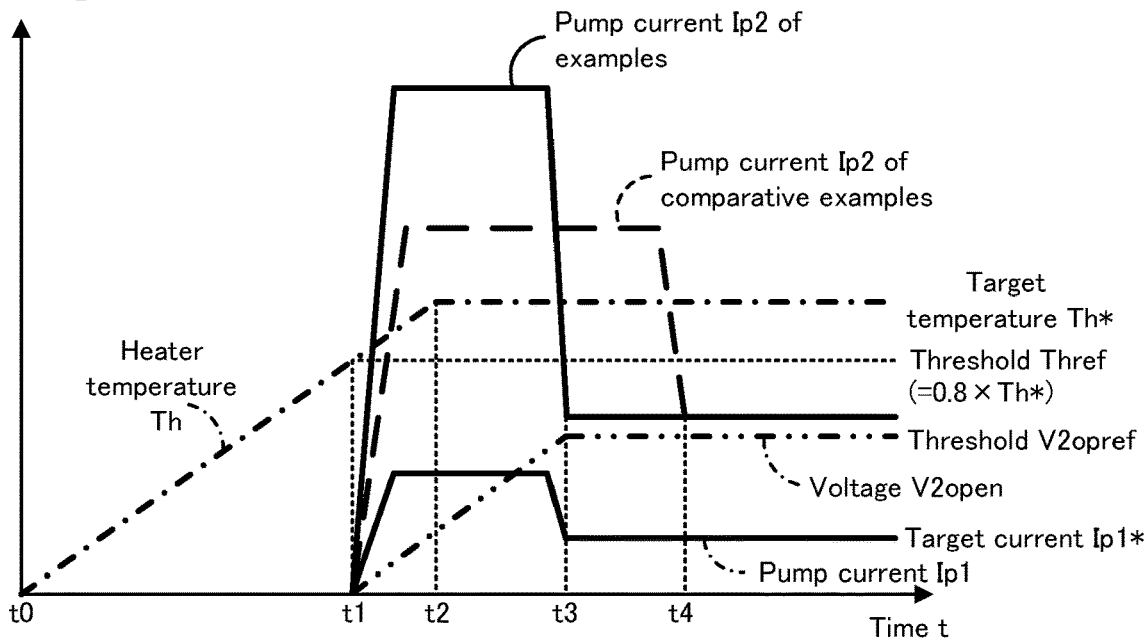
FIG. 6 is a graph showing an example of behavior of a start-up time control process and a normal time control process of a modification.

The CPU 92 may determine whether or not the termination condition for the start-up time measurement pump control process is satisfied, based on an open time measurement voltage V2*open* which is the voltage V2 in a state in which no control is performed to pass a current through the measurement electrode 44 and the reference electrode 42. FIG. 5 is a flowchart showing an example of a start-up time control process of a modification. FIG. 6 is a graph showing an example of behavior of a start-up time control process and a normal time control process of a modification. In FIG. 5, the same process as in FIG. 3 is labeled with the same step number, and a description thereof is omitted. FIG. 6 shows FIG. 4 and an additionally illustrated manner of time change of the open time measurement voltage V2*open*. In the start-up time control process of a modification shown in FIG. 5, after the start-up time measurement pump control process is started in step S120, the CPU 92 determines whether or not the termination condition for the start-up time measurement pump control process is satisfied by determining whether or not the open time measurement voltage V2*open* has reached a level higher than or equal to a predetermined threshold V2*opref* (step S230), the V2*open* being the voltage V2 in a state in which no control is performed to pass a current through the measurement electrode 44 and the reference electrode 42. For example, in the above-described embodiment, no control is performed to pass a current through the reference electrode 42, and after the start-up time measurement pump control process is started in step S120, the pump current Ip2 is caused to flow through the measurement electrode 44 by the start-up time measurement pump control process. Thus, the CPU 92 measures the voltage V2 in step S230 in a state in which the start-up time measurement pump control process is temporarily stopped, specifically, in a state in which application of the voltage Vp2 from the variable power supply 46 is stopped, and sets the open time measurement voltage V2*open* to the measured value. The open time measurement voltage V2*open* is a value corresponding to the oxygen concentration in the third internal cavity 61, and has a greater value for a lower oxygen concentration. The open time measurement voltage V2*open* is measured in a state in which no control is performed to pass a current through the measurement electrode 44 and the reference electrode 42, thus is unlikely to be affected by voltage drop due to a current. Thus, the open time measurement voltage V2*open* has a value which corresponds to the oxygen concentration in the third internal cavity 61 with higher accuracy than the voltage V2 (the voltage V2 during execution of the start-up time measurement pump control process) measured in a state in which control is performed to pass a current through the measurement electrode 44. The threshold V2*opref* is defined in advance as the value of the open time measurement voltage V2*open* in a state in which the oxygen in the third internal cavity 61 is sufficiently pumped out. For example, as shown in FIG. 6, when the start-up time measurement pump control process is started, the value of the open time measurement voltage V2*open* is increased, and has a substantially constant value (steady-state value) after time t3 when pumping out of the oxygen, which has been present in the third internal cavity 61 since before the start-up, is completed, in other words, after the time when the sensor element 101 is lighted off. In the present embodiment, the steady-state value measured in advance by an experiment is defined as the threshold V2*opref*. In the present embodiment, the threshold V2*opref* is set to 200 mV.

The threshold V2opref may have a value slightly lower than the steady-state value of the open time measurement voltage V2open. When a negative determination is made in step S230, the CPU 92 repeatedly executes step S230 until an affirmative determination is made. When an affirmative determination is made in step S230, the CPU 92 executes step S140 described above to terminate the start-up time control process. As described above, the open time measurement voltage V2open has a value that corresponds to the oxygen concentration in the third internal cavity 61, thus, it is possible to appropriately determine whether or not the oxygen in the third internal cavity 61 has been sufficiently pumped out by comparing the open time measurement voltage V2open with the threshold V2opref. Thus, even when the CPU 92 executes step S230 in FIG. 5 instead of step S130 in FIG. 3, switching from the start-up time measurement pump control process to the normal time measurement pump control process can be appropriately made. Note that as described above, the time when the pump current Ip1 is stabilized at around the target current Ip1* may be slightly earlier than the time t3 when the sensor element 101 is lighted off. In contrast, unlike the pump current Ip1, the open time measurement voltage V2open has a value corresponding to the oxygen present in the third internal cavity 61 itself, thus there is hardly no difference between the time when the open time measurement voltage V2open reaches a steady-state value, and the time when the sensor element 101 is lighted off.

In the embodiment described above, in the start-up time measurement pump control process, the oxygen in the third internal cavity 61 is pumped out to the surroundings of the outer pump electrode 23; however, the oxygen may be pumped out to the surroundings of an electrode disposed at a position other than the measurement-object gas flow portion, not limited to the surroundings of the outer pump electrode 23. For example, in the start-up time measurement pump control process, the oxygen in the third internal cavity 61 may be pumped out to the surroundings of the reference electrode 42 by passing a pump current by application of a voltage between the measurement electrode 44 and the reference electrode 42. That is, in the start-up time measurement pump control process of the above-described embodiment, the oxygen in the third internal cavity 61 is pumped out to the outside of the element body, the outside being the surroundings of the outer pump electrode 23. However, the oxygen may be pumped out to the inside of the element body, such as the surroundings of the reference electrode 42. When the oxygen is pumped out to the inside of the element body, it is preferable that the oxygen be pumped out to the surroundings of an electrode, such as the reference electrode 42, disposed at a position other than the measurement-object gas flow portion. In other words, when the oxygen is pumped out to the inside of the element body, it is preferable that the oxygen be pumped out to an area of the element body, the area not communicating with the third internal cavity 61.

Although a description has not been given particularly in the above-described embodiment, it is preferable that the voltage Vp2 applied to the measurement pump cell 41 be lower than 1500 mV. When the voltage Vp2 is higher than or equal to 1500 mV, the oxygen ions in the solid electrolyte may become deficient, and electronic conduction in the solid electrolyte may occur, then the sensor element 101 may be blackened to become unusable; however, such a problem can be avoided by setting the voltage Vp2 lower than 1500 mV. The higher the value of the start-up time target value V2a*, the higher the value of the voltage Vp2 at the time of the start-up time measurement pump control process. Thus, it is preferable that the start-up time target value V2a* be defined as a value which prevents the voltage Vp2 from exceeding 1500 mV. When the start-up time measurement pump control process is executed in a state in which the solid electrolyte is not sufficiently activated, the oxygen in the third internal cavity 61 is not pumped out and the voltage V2 does not approach the start-up time target value V2a*, thus the voltage Vp2 tends to have a high value due to feedback control. Therefore, when the start-up time measurement pump control process is executed in a state in which the solid electrolyte is not sufficiently activated, the voltage Vp2 tends to be higher than or equal to 1500 mV during the start-up time measurement pump control process. In consideration of this point, it is preferable that the start condition (the value of the threshold Thref in the above-described embodiment) for the start-up time measurement pump control process be appropriately defined so that the voltage Vp2 does not exceed 1500 mV.

In the heater control process of the above-described embodiment, the CPU 92 controls the heater 72 so that the heater temperature Th reaches the target temperature Th*; however, without using the heater temperature Th, the CPU 92 may control the heater 72 so that the sensor element temperature, which is the temperature of the heater 72 or the element body, reaches a target temperature. For example, the resistance value of the circuit of the measurement pump cell 41 or the resistance value of the circuit of the measurement pump control oxygen partial pressure detection sensor cell 82 is measured as the value (value convertible to the temperature) representing the temperature of the element body, and the heater 72 may be controlled so that the resistance value reaches a target resistance value. Similarly, in the above-described embodiment, when the heater temperature Th reaches a level higher than or equal to the predetermined threshold Thref, the start-up time measurement pump control process is started; however, the configuration is not limited thereto. When the sensor element temperature in addition to the heater temperature Th reaches a level higher than or equal a predetermined threshold (for example, when the resistance value of the circuit of the measurement pump cell 41 reaches a level lower than or equal to a predetermined threshold), the start-up time measurement pump control process may be started. Alternatively, the gas sensor 100 may include a temperature detector such as a thermocouple, and the temperature sensor may directly measure the sensor element temperature (the temperature of the heater 72 or the temperature of the element body) itself. In this case, the CPU 92 may control the heater 72 in accordance with the measured sensor element temperature so that the sensor element temperature reaches a target temperature.

In the above-described embodiment, when the heater temperature Th reaches a level higher than or equal to the predetermined threshold Thref, the CPU 92 determines that the start condition for the start-up time measurement pump control process is satisfied; however, the configuration is not limited thereto. The start condition for the start-up time measurement pump control process may be defined so that the start-up time measurement pump control process can be started when the solid electrolyte contained in the measurement pump cell 41 controlled by the start-up time measurement pump control process is activated. For example, when a predetermined time has elapsed since the start of energization of the heater 72, the start-up time measurement pump control process may be started.

Figure 7:
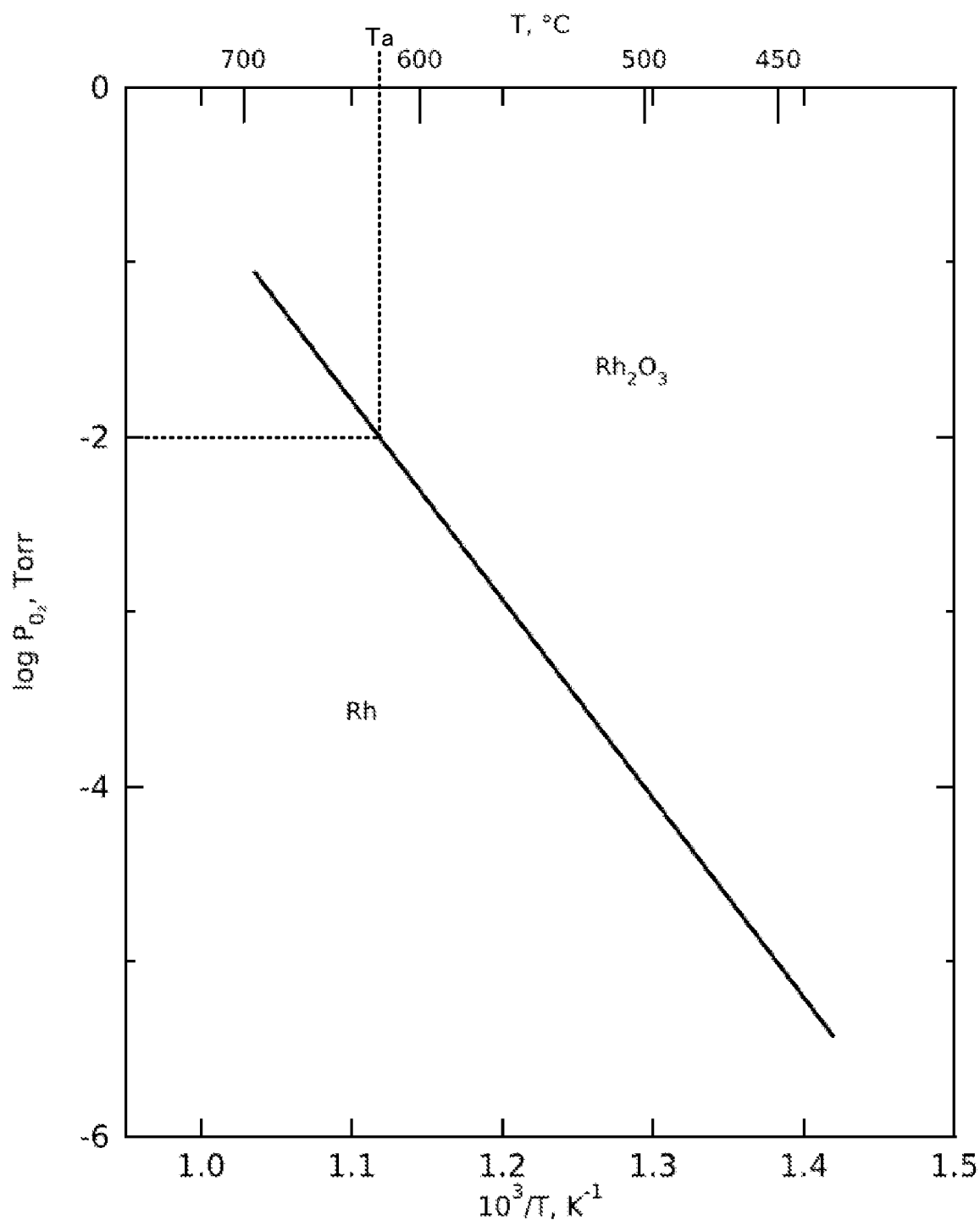
FIG. 7 is a phase diagram of $Rh_2O_3$.

Alternatively, the start condition for the start-up time measurement pump control process may be defined so that the start-up time measurement pump control process can be started when a state suitable for pumping out the oxygen binding to the constituent material is achieved according to the constituent material for the measurement electrode 44. For example, the start condition for the start-up time measurement pump control process may be defined based on the phase diagram of the constituent material for the measurement electrode 44. An example of a start condition when the measurement electrode 44 contains Rh as the constituent material will be described. FIG. 7 is a phase diagram of $Rh_2O_3$ (references: V. K. Tagirov, D. M. Chizhikov, E. K. Kazenas, and L. K. S hubochkin, Zh. Neorg. Khim., Title: Study of thermal dissociation of ruthenium dioxide and rhodium sesquioxide, Journal: Zhurnal Neorganicheskoj Khimii; v.20(8); p. 2035-2037 (1975)). The vertical axis of FIG. 7 indicates oxygen partial pressure, and the horizontal axis thereof indicates temperature. The thick straight line in FIG. 7 is a straight line (equilibrium line) showing a relationship between oxygen partial pressure and temperature, in which $Rh_2O_3$ and Rh are in an equilibrium state. The start condition for the start-up time measurement pump control process may be defined based on the equilibrium line so that the start-up time measurement pump control process is executed in a state suitable for reduction of the oxide (here, $Rh_2O_3$) of the constituent material (here, Rh) for the measurement electrode 44 (specifically, a state in which a corresponding point between temperature and oxygen partial pressure is located in an area in the lower left of the equilibrium line in FIG. 7). For example, when the logarithm ($\log P_{O2}$) of the oxygen partial pressure in the third internal cavity 61, corresponding to the start-up time target value V2$a$* for the start-up time measurement pump control process is −2 (equivalently, when the oxygen partial pressure is 0.01 Torr), as shown by the dotted line added to the phase diagram of FIG. 7, the temperature of the measurement electrode 44 corresponding to the oxygen partial pressure on the equilibrium line is Ta° C. (approximately 630° C.). Thus, when the voltage V2 is at around the start-up time target value V2$a$* and the temperature of the measurement electrode 44 is higher than or equal to Ta° C. due to the start-up time measurement pump control process, $Rh_2O_3$ is likely to be reduced to Rh. Thus, the start condition for the start-up time measurement pump control process may be defined so that the start-up time measurement pump control process can be started when the temperature of the measurement electrode 44 reaches a level higher than or equal to Ta° C. For example, the threshold Thref may be determined as the lower limit value of the heater temperature Th which is needed to cause the temperature of the measurement electrode 44 to reach a level higher than or equal to Ta° C. Alternatively, when a predetermined time has elapsed since the start of energization of the heater 72, the start-up time measurement pump control process may be started, and the predetermined time may be defined based on the time taken for the temperature of the measurement electrode 44 to reach a level higher than or equal to Ta° C. since the start of the heater control process. Note that as seen from FIG. 7, the higher the temperature of the measurement electrode 44 and the lower the oxygen partial pressure in the third internal cavity 61, $Rh_2O_3$ is more likely to be reduced. In other words, the lower the oxygen partial pressure in the third internal cavity 61, the lower the temperature of the measurement electrode 44 suitable for starting the start-up time measurement pump control process. Therefore, when the start-up time target value V2$a$* is set to a higher value, the start-up time measurement pump control process can be started in a short time accordingly from the start of the heater control process. However, as described above, it is preferable that the start-up time target value V2$a$* be defined as a value which prevents the voltage Vp2 from exceeding 1500 mV. In consideration of this point also, it is preferable that the start-up time target value V2$a$* be set to a value which is not too high. As described above, the start-up time measurement pump control process is preferably executed after the solid electrolyte is activated, thus it is preferable that the start condition for the start-up time measurement pump control process be defined based on the temperature higher between the temperature needed to activate the solid electrolyte, and the temperature suitable for reduction of the oxide of the constituent material for the measurement electrode 44. Even when the measurement electrode 44 contains Pt as the constituent material, similarly to the above-described example, the start condition for the start-up time measurement pump control process suitable for reduction of the oxide of Pt may be defined based on the phase diagram of Pt. When the measurement electrode 44 contains both Pt and Rh as the constituent material, it is preferable that the start condition for the start-up time measurement pump control process be defined based on the temperature higher between the temperature suitable for reduction of the oxide of Pt and the temperature suitable for reduction of the oxide of Rh.

In the above-described embodiment, the CPU 92 starts the adjustment pump control process (the main pump control process and the auxiliary pump control process) at the same time as starting the start-up time measurement pump control process; however, the configuration is not limited thereto. A time difference may be given between a timing for starting the adjustment pump control process and a timing for starting the start-up time measurement pump control process. The adjustment pump cell (the main pump cell 21 and the auxiliary pump cell 50) has a higher ability to pump out oxygen than the measurement pump cell 41, thus it is preferable that the adjustment pump control process (the main pump control process and the auxiliary pump control process) be started at the same time as or earlier than the start of the start-up time measurement pump control process. In addition, during the start-up time measurement pump control process, the adjustment pump control process (the main pump control process and the auxiliary pump control process) is also preferably executed.

In the above-described embodiment, the oxygen concentration adjustment chamber has the first internal cavity 20 and the second internal cavity 40; however, the configuration is not limited thereto, and for example, the oxygen concentration adjustment chamber may have another internal cavity, or one of the first internal cavity 20 and the second internal cavity 40 may be omitted. Similarly, in the above-described embodiment, the adjustment pump cell has the main pump cell 21 and the auxiliary pump cell 50; however, the configuration is not limited thereto, and for example, the adjustment pump cell may have another pump cell, or one of the main pump cell 21 and the auxiliary pump cell 50 may be omitted. For example, when the oxygen concentration in a measurement-object gas can be sufficiently reduced only by the main pump cell 21, the auxiliary pump cell 50 may be omitted. In this case, as the adjustment pump control process, the CPU 92 may execute a process to control the main pump cell 21 so that the oxygen concentration in the oxygen concentration adjustment chamber (the first internal cavity 20) reaches a target concentration, for example. More specifically, a target value V0* may be defined in advance, and the CPU 92 may control the main pump cell 21 by executing feedback control on the pump voltage Vp0 of the variable power supply 24 so that the voltage V0 reaches the target value V0* (in other words, so that the oxygen concentration in the first internal cavity 20 reaches a target concentration). In this case, when determining that the oxygen concentration in the first internal cavity 20 is stabilized based on the operation of the main pump cell 21, the CPU 92 may make switching from the start-up time measurement pump control process to the normal time measurement pump control process. For example, the CPU 92 may determine whether or not the oxygen concentration in the first internal cavity 20 is stabilized based on the value of the voltage V0 or the value of the pump current Ip0. More specifically, when the voltage V0 reaches a level higher than or equal to a predetermined threshold, the CPU 92 may determine that the oxygen concentration in the first internal cavity 20 is stabilized, and when the pump current Ip0 is once increased and decreased to a level lower than or equal to a predetermined threshold, the CPU 92 may determine that the oxygen concentration in the first internal cavity 20 is stabilized.

In the above-described embodiment, the outer pump electrode 23 serves as an outer main pump electrode, an outer auxiliary pump electrode, and an outer measurement electrode, the outer main pump electrode being disposed in a portion which is part of the main pump cell 21 and exposed to a measurement-object gas outside the sensor element 101, the outer auxiliary pump electrode disposed in a portion which is part of the auxiliary pump cell 50 and exposed to a measurement-object gas outside the sensor element 101, the outer measurement electrode disposed in a portion which is part of the measurement pump cell 41 and exposed to a measurement-object gas outside the sensor element 101; however, the configuration is not limited thereto. In addition to the outer pump electrode 23, one or more of the outer main pump electrode, the outer auxiliary pump electrode, and the outer measurement electrode may be provided outside the sensor element 101.

In the above-described embodiment, the outer pump electrode 23 is exposed to the outside of the sensor element 101; however, the configuration is not limited thereto, and the outer pump electrode 23 may be provided outside the element bodies (layers 1 to 6) so as to be in contact with a measurement-object gas. For example, the sensor element 101 may include a porous protective layer that covers the element bodies (layers 1 to 6), and the outer pump electrode 23 may also be covered with the porous protective layer.

Figure 8:
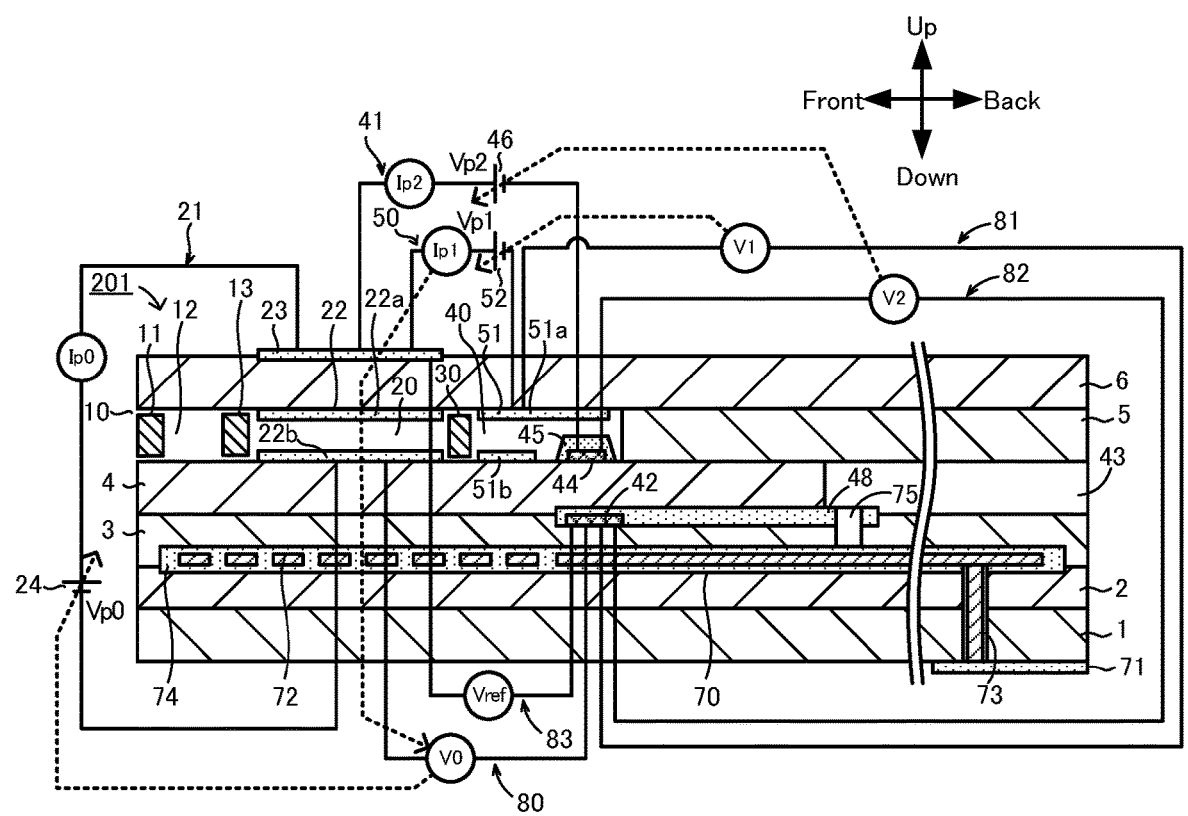
FIG. 8 is a schematic cross-sectional view of a sensor element 201 of a modification.

In the above-described embodiment, the sensor element 101 of the gas sensor 100 includes the first internal cavity 20, the second internal cavity 40, and the third internal cavity 61; however, the configuration is not limited thereto. For example, as in the case of a sensor element 201 of FIG. 8, the third internal cavity 61 may be omitted. In the sensor element 201 of a modification shown in FIG. 8, the gas inlet port 10, the first diffusion controlled portion 11, the buffer space 12, the second diffusion controlled portion 13, the first internal cavity 20, the third diffusion controlled portion 30, and the second internal cavity 40 are formed adjacent to each other in this order between the under surface of the second solid electrolyte layer 6 and the top surface of the first solid electrolyte layer 4 so as to communicate with each other. The measurement electrode 44 is disposed on the top surface of the first solid electrolyte layer 4 in the second internal cavity 40. The measurement electrode 44 is coated with a fourth diffusion controlled portion 45. The fourth diffusion controlled portion 45 is a film made up of a ceramic porous material, such as alumina ($Al_2O_3$). The fourth diffusion controlled portion 45, as well as the fourth diffusion controlled portion 60 of the above-described embodiment, plays a role in limiting the amount of NOx flowing into the measurement electrode 44. The fourth diffusion controlled portion 45 also functions as a protection film for the measurement electrode 44. The ceiling electrode portion 51*a* of the auxiliary pump electrode 51 is formed up to just above the measurement electrode 44. With the thus configured sensor element 201 as well, it is possible to detect a NOx concentration in accordance with, for example, a pump current Ip2 as in the case of the above-described embodiment. In this case, the surroundings of the measurement electrode 44 function as a measurement chamber.

In the above-described embodiment, the element body of the sensor element 101 is a layered body including a plurality of solid electrolyte layers (layers 1 to 6); however, the configuration is not limited thereto. The element body of the sensor element 101 may include at least one oxygen-ion-conductive solid electrolyte layer and include a measurement-object gas flow portion inside. For example, the layers 1 to 5 other than the second solid electrolyte layer 6 in FIG. 1 may be a structural layer made of a material other than a solid electrolyte (for example, a layer made of alumina). In this case, the electrodes of the sensor element 101 just need to be disposed on the second solid electrolyte layer 6. For example, the measurement electrode 44 of FIG. 1 just needs to be disposed on the under surface of the second solid electrolyte layer 6. The reference gas inlet space 43 may be provided in the spacer layer 5 instead of the first solid electrolyte layer 4, the atmosphere inlet layer 48 may be provided between the second solid electrolyte layer 6 and the spacer layer 5 instead of being provided between the first solid electrolyte layer 4 and the third substrate layer 3, and the reference electrode 42 may be provided on the rear side with respect to the third internal cavity 61 on the under surface of the second solid electrolyte layer 6.

In the above-described embodiment, in the main pump control process, the control apparatus 90 sets (executes feedback control on) the target value V0* of the voltage V0 based on the pump current Ip1 so that the pump current Ip1 reaches a target value Ip1* and executes feedback control on the pump voltage Vp0 so that the voltage V0 reaches a target value V0*; however, another control may be employed. For example, in the main pump control process, the control apparatus 90 may execute feedback control on the pump voltage Vp0 in accordance with the pump current Ip1 so that the pump current Ip1 reaches a target value Ip1*. In other words, the control apparatus 90 may directly control the pump voltage Vp0 (by extension, control the pump current Ip0) in accordance with the pump current Ip1 by omitting acquisition of the voltage V0 from the main pump control oxygen partial pressure detection sensor cell 80 and setting of the target value V0*. In this case, the CPU 92 can determine whether or not the termination condition for the start-up time measurement pump control process is satisfied by using, for example, the process in the above-described step S130 of FIG. 3 or step S230 of FIG. 5.

In the above-described embodiment, the gas sensor 100 detects a NOx concentration as a specific gas concentration; however, the configuration is not limited thereto. Another oxide concentration may be used as a specific gas concentration. In the case where the specific gas is an oxide, oxygen is produced when the specific gas itself is reduced in the third internal cavity 61 as in the case of the above-described embodiment, so the CPU 92 is able to detect a specific gas concentration based on a detected value corresponding to the oxygen. Alternatively, the specific gas may be a non-oxide, such as ammonia. When the specific gas is a non-oxide, the specific gas is converted to an oxide, for example, in the first internal cavity 20 (for example, ammonia is oxidized and converted to NO), and oxygen is produced when the oxide after conversion is reduced in the third internal cavity 61, so the CPU 92 is able to detect a specific gas concentration by acquiring a detected value corresponding to the oxygen. In this manner, in whichever case the specific gas is an oxide or a non-oxide, the gas sensor 100 is able to detect a specific gas concentration based on the oxygen produced from a specific gas in the third internal cavity 61.

In the above-described embodiment, the value of the start-up time target value V2$a$* may be set according to the volume of the measurement electrode 44. The inventors have found that the light-off time may vary depending on the volume of the measurement electrode 44 even with the same start-up time target value V2$a$*; if the value of the start-up time target value V2$a$* is too high or too low, the effect of reducing the light-off time may decrease, and an optimal value of the start-up time target value V2$a$* exists; and when the volume of the measurement electrode 44 changes, the optimal value of the start-up time target value V2$a$* also changes. This will be described in detail in the following.

Figure 9:
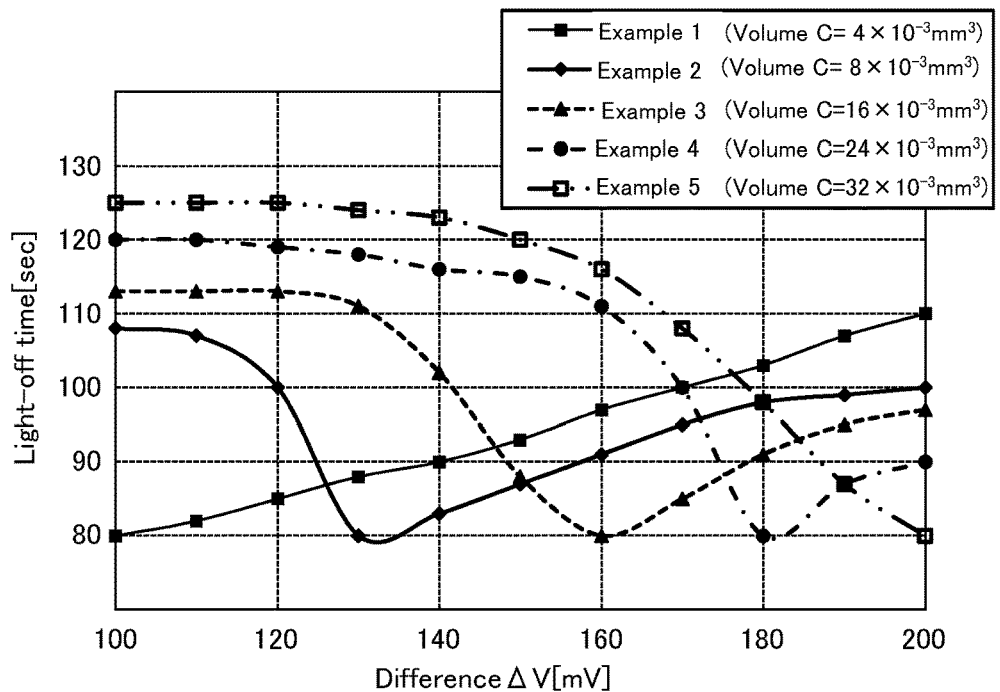
FIG. 9 is a graph showing the relationship between volume C of a measurement electrode 44, difference ΔV and light-off time, the difference ΔV being between target values.

The inventors have studied the relationship between volume C of the measurement electrode 44 [mm$^3$], difference ΔV (=V2$a$*−V2$b$*) [mV] between the start-up time target value V2$a$* and the normal time target value V2$b$*, and light-off time [sec] in the following manner. First, Experimental Example 1 was prepared by the sensor element 101 and the gas sensor 100 of above-described embodiment explained using FIGS. 1 and 2. Volume C of the measurement electrode 44 in Experimental Example 1 was 4×10$^{-3}$ mm$^3$. As described above, the measurement electrode 44 is a porous cermet electrode containing Pt, Rh, and ZrO$_2$. In addition, Experimental Examples 2 to 5 were prepared by the same gas sensor 100 as in Experimental Example 1 except that various changes are made on volume C as shown in Table 1 by changing the thickness and the length in the front-back direction of the measurement electrode 44. Specifically, the thickness of the measurement electrode 44 in Experimental Example 2 is twice the thickness in Experimental Example 1. The thickness of the measurement electrode 44 in Experimental Example 3 is twice the thickness in Experimental Example 2. The thickness and the length in the front-back direction of the measurement electrode 44 in Experimental Example 4 are 1.5 times the thickness and twice the length in Experimental Example 2. The thickness and the length in the front-back direction of the measurement electrode 44 in Experimental Example 5 are twice the thickness and twice the length in Experimental Example 2. For the gas sensor 100 in Experimental Example 1, the start-up time target value V2$a$* was set to 500 mV, the normal time target value V2$b$* was set to 400 mV (therefore, the difference ΔV was 100 mV), and the light-off time was measured when the start-up time control process shown in FIG. 3 is executed. Similarly, in the gas sensor 100 in Experimental Example 1, the difference ΔV was changed by 10 mV each time between 110 mV and 200 mV as shown in Table 1 by changing the start-up time target value V2$a$*, and the light-off time in each case was measured. Also, in the gas sensor 100 in Experimental Examples 2 to 5, the difference ΔV was changed similarly between 100 mV and 200 mV, and the light-off time in each case was measured. Table 1 collectively shows volume C of the measurement electrode 44, and the light-off time corresponding to the difference ΔV (=V2$a$*−V2$b$*) between the start-up time target value V2$a$* and the normal time target value V2$b$* in each of Experimental Example 1 to 5. FIG. 9 is a graph generated from Table 1, and the graph shows a relationship between the volume C of the measurement electrode 44, the difference ΔV, and the light-off time. Note that in each of Experimental Example 1 to 5, when the difference ΔV is within a range of 100 mV to 200 mV, the light-off time is shorter than when the start-up time measurement pump control process is not executed (in other words, when the difference ΔV is 0 mV). Thus, each of Experimental Example 1 to 5 corresponds to Example of the present invention.

TABLE 1

| Difference ΔV | Experimental Example 1 | Experimental Example 2 | Experimental Example 3 | Experimental Example 4 | Experimental Example 5 |
| --- | --- | --- | --- | --- | --- |
| | Volume C of measurement electrode [× 10$^{-3}$ mm$^3$] | | | | |
| (= V2$a$* − V2$b$*) [mV] | 4 | 8 | 16 | 24 | 32 |
| | Light-off time[sec] | | | | |
| 100 | 80 | 108 | 113 | 120 | 125 |
| 110 | 82 | 107 | 113 | 120 | 125 |
| 120 | 85 | 100 | 113 | 119 | 125 |
| 130 | 88 | 80 | 111 | 118 | 124 |
| 140 | 90 | 83 | 102 | 116 | 123 |
| 150 | 93 | 87 | 88 | 115 | 120 |
| 160 | 97 | 91 | 80 | 111 | 116 |
| 170 | 100 | 95 | 85 | 100 | 108 |
| 180 | 103 | 98 | 91 | 80 | 98 |
| 190 | 107 | 99 | 95 | 87 | 87 |
| 200 | 110 | 100 | 97 | 90 | 80 |

As seen from Table 1 and FIG. 9, it has been verified that the light-off time is not necessarily shorter for a larger difference ΔV, in other words, the light-off time is not necessarily shorter for a higher start-up time target value V2$a$*. For example, in Experimental Example 3, it has been verified that the light-off time is the shortest when the difference ΔV is 160 mV, and the light-off time tends to increase when the difference ΔV is lowered or raised from 160 mV. For Experimental Examples 2, 4 also, the same tendency has been verified. In Experimental Example 1, when the difference ΔV is within a range of 100 mV to 200 mV, the light-off time tends to be longer for a larger difference ΔV. Therefore, in Experimental Example 1, it is presumed that the value of the difference ΔV that achieves the shortest light-off time is less than 100 mV. In Experimental Example 5, when the difference ΔV is within a range of 100 mV to 200 mV, the light-off time tends to be shorter for a larger difference ΔV. Therefore, in Experimental Example 5, it is presumed that the value of the difference ΔV that achieves the shortest light-off time is greater than 200 mV.

Figure 10:
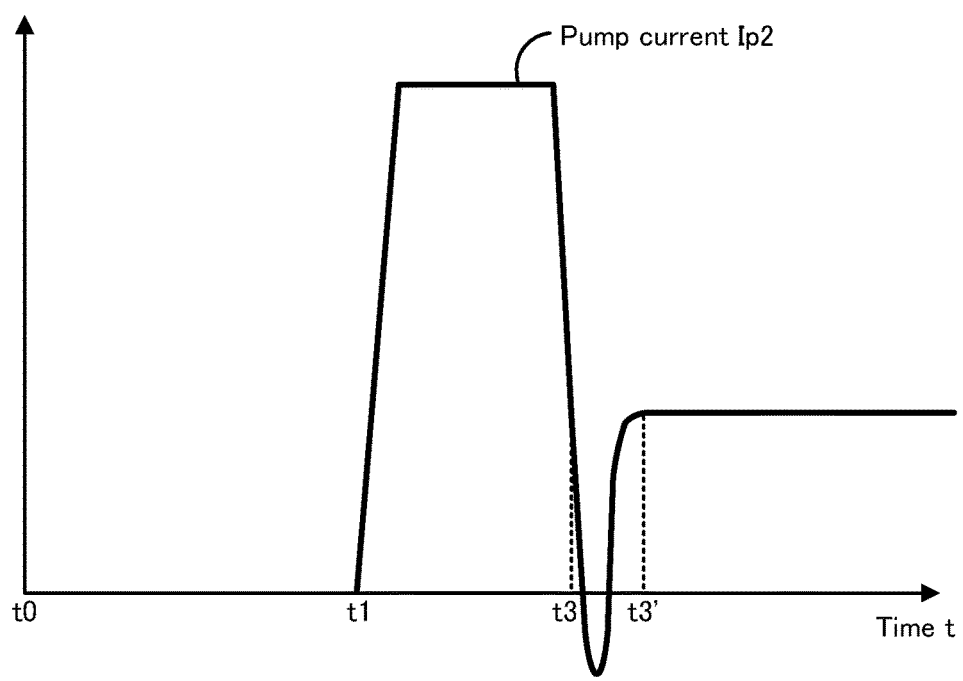
FIG. 10 is a graph showing an example of undershoot of a pump current Ip2.

The reason why the relationship between the volume C of the measurement electrode 44, the difference ΔV, and the light-off time has the above-mentioned tendency will be described. First, the inventors have found that when switching is made from the start-up time measurement pump control process to the normal time measurement pump control process, undershoot of the pump current Ip2 may occur. FIG. 10 is a graph showing an example of undershoot of the pump current Ip2. Times t0, t1, t3 in FIG. 10 are the same as those shown in FIG. 4. As shown in FIG. 10, when switching is made from the start-up time measurement pump control process to the normal time measurement pump control process at time t3, the pump current Ip2 may not immediately take a value corresponding to the NOx concentration in a measurement-object gas, but undershoot of the pump current Ip2 may occur, and after subsequent time t3', the value of the pump current Ip2 may take a value corresponding to the NOx concentration in the measurement-object gas. The light-off time in this case is the time period from time t0 to time t3', thus the light-off time is increased by the period (time t3 to t3') in which undershoot occurs.

The reason why such an undershoot occurs is probably as follows. When switching is made from the start-up time measurement pump control process to the normal time measurement pump control process, the target value of the voltage V2 is changed from the start-up time target value V2$a$* to the normal time target value V2$b$* (<V2$a$*), thus the oxygen concentration in the third internal cavity 61 immediately after the switching may be lower than the oxygen concentration corresponding to the normal time target value V2$b$*. Thus, immediately after the switching to the normal time measurement pump control process, in order to increase the oxygen concentration in the third internal cavity 61 up to the oxygen concentration corresponding to the normal time target value V2$b$*, the controller 91 may control the measurement pump cell 41 not to pump out oxygen from the third internal cavity 61, but to pump oxygen into the third internal cavity 61. In this case, the pump current Ip2 has a negative value (positive and negative are reversed for the pump current Ip2 during the start-up time measurement pump control process). In addition, during the start-up time measurement pump control process, the water in a measurement-object gas may be decomposed due to the voltage Vp2 applied to the measurement electrode 44, and hydrogen may be produced. After switching is made to the normal time measurement pump control process, reaction of the hydrogen with oxygen causes the oxygen concentration in the third internal cavity 61 to decrease, thus this also may cause the pump current Ip2 to decrease or have a negative value. The greater the volume C of the measurement electrode 44, the larger the surface area (includes not only the outer surface of the measurement electrode 44, but also the surface area of the pores inside the measurement electrode 44) of the measurement electrode 44, thus the greater the volume C, the amount of hydrogen produced during the start-up time measurement pump control process tends to increase. Based upon the foregoing, the greater the difference ΔV (=V2$a$*−V2$b$*) and the volume C, the longer the period of occurrence of undershoot which appears when switching is made from the start-up time measurement pump control process to the normal time measurement pump control process, thus the light-off time tends to increase.

In addition, for a greater difference ΔV (=V2$a$*−V2$b$*), the oxygen which has been present in the third internal cavity 61 since before the start-up of the sensor element 101 can be quickly removed in the start-up time measurement pump control process. Therefore, the greater the difference ΔV (=V2$a$*−V2$b$*), the shorter the time period (for example, time t1 to t3 in FIG. 10) in which the start-up time measurement pump control process is executed, thus the light-off time tends to be short. For a shorter total time of the time period (for example, time t1 to t3 in FIG. 10) in which the start-up time measurement pump control process is executed, and the time period (for example, time t3 to t3' in FIG. 10) in which undershoot occurs, the light-off time (for example, time t0 to t3' in FIG. 10) can be reduced.

Based upon the foregoing, when the value of the start-up time target value V2$a$*, more accurately, the difference ΔV is too small, the time period in which the start-up time measurement pump control process is executed is increased (the time taken to pump out the oxygen which has been present in the third internal cavity 61 since before the start-up is increased), thus the effect of shortening the light-off time is probably reduced. If the difference ΔV is too large, the time period in which undershoot occurs increases, thus the effect of shortening the light-off time is probably reduced. Thus, an optimal difference ΔV probably exists, which provides the greatest effect of shortening the light-off time for a certain sensor element 101. As mentioned above, the time period in which undershoot occurs varies depending on the volume C of the measurement electrode 44, thus when the volume C is changed, the optimal difference ΔV providing the greatest effect of shortening the light-off time is also changed.

Specifically, for a greater volume C, the optimal difference ΔV probably tends to increase. Because of the above-mentioned reasons, the relationship between the volume C of the measurement electrode 44, the difference ΔV, and the light-off time is as shown in Table 1 and FIG. 9.

Here, the volume C of the measurement electrode 44 is preferably greater than or equal to $8 \times 10^{-3}$ mm$^3$. When the volume C is greater than or equal to $8 \times 10^{-3}$ mm$^3$, the ability to pump out the oxygen in the surroundings of the measurement electrode 44 by the measurement pump cell 41 is sufficiently high. Therefore, Experimental Examples 2 to 5, in which the volume C is greater than or equal to $8 \times 10^{-3}$ mm$^3$, are more preferable than Experimental Example 1. If the difference ΔV is too large, the voltage Vp2 at the time of the start-up time measurement pump control process has a high value, and as described above, the sensor element 101 may be blackened to become unusable. If the voltage Vp2 at the time of the start-up time measurement pump control process is too high, application of an excessive voltage Vp2 to the measurement electrode 44 may cause deterioration of the measurement electrode 44 and increase in the resistance value of the measurement electrode 44, thus the sensitivity of detection of NOx concentration may be reduced.

Therefore, the difference ΔV is preferably less than or equal to 200 mV. From the result in FIG. 9, with the volume C greater than the volume in Experimental Example 5, when the difference ΔV is in a range lower than or equal to 200 mV, the effect of shortening the light-off time is presumably reduced. Therefore, the volume C is preferably less than or equal to the volume in Experimental Example 5, specifically, less than or equal to $32 \times 10^{-3}$ mm$^3$. As a range in which the light-off time can be set to a minimum value or its approximate value in Experimental Examples 2 to 5, and in which the difference ΔV not exceed 200 mV, the difference ΔV is preferably 120 mV or more and 200 mV or less. Based upon the foregoing, the volume C is preferably $8\times10^{-3}$ mm$^3$ or more and $32\times10^{-3}$ mm$^3$ or less, and the difference ΔV is preferably 120 mV or more and 200 mV or less. For a greater volume C, the difference ΔV needed to sufficiently enhance the effect of shortening the light-off time tends to increase; however, when the volume C is $8\times10^{-3}$ mm$^3$ or more and $32\times10^{-3}$ mm$^3$ or less, and the difference ΔV is 120 mV or more and 200 mV or less, the effect of shortening the light-off time can be sufficiently enhanced while satisfying the lower limit value of the volume C and the upper limit value of the difference ΔV mentioned above.

Note that when the volume C of the measurement electrode 44 is adjusted, the thickness of the measurement electrode 44 may be, for example, 10 μm or more and 40 μm or less. The area of the top surface of the measurement electrode 44, in other words, the product of the crosswise width and the front-back length of the measurement electrode 44 may be 0.2 mm$^2$ or more and 1.2 mm$^2$ or less. The crosswise width of the measurement electrode 44 may be 0.5 mm or more and 2.5 mm or less. When the difference ΔV is adjusted, the start-up time target value $V2a^*$ is preferably lower than or equal to 600 mV.

What is claimed is:

1. A gas sensor comprising:
    a sensor element including
       an element body which includes an oxygen-ion-conductive solid electrolyte layer, and is internally provided with a measurement-object gas flow portion that introduces a measurement-object gas and flows the measurement-object gas,
       a measurement pump cell having an outer measurement electrode provided outside the element body to be in contact with the measurement-object gas, and an inner measurement electrode disposed in a measurement chamber of the measurement-object gas flow portion, the measurement pump cell being configured to pump out oxygen from surroundings of the inner measurement electrode to surroundings of the outer measurement electrode,
       a reference electrode disposed inside the element body to come into contact with a reference gas which serves as a reference for detection of a specific gas concentration in the measurement-object gas, and
       a measurement voltage detection sensor cell that detects a measurement voltage between the reference electrode and the inner measurement electrode;
    a pump cell controller that executes a normal time measurement pump control process of pumping out oxygen in the measurement chamber during a normal operation time of the sensor element by controlling the measurement pump cell so that the measurement voltage reaches a normal time target value, and executes a start-up time measurement pump control process of pumping out oxygen in the measurement chamber at a start-up time of the sensor element earlier than the normal operation time by controlling the measurement pump cell so that the measurement voltage reaches a start-up time target value higher than the normal time target value; and
    a specific gas concentration detection section that detects the specific gas concentration in the measurement-object gas based on a measurement pump current which flows through the measurement pump cell by the normal time measurement pump control process.

2. The gas sensor according to claim 1, further comprising:
    a heater that heats the element body; and
    a heater controller that executes a heater control process of energizing the heater to cause the heater to generate heat so that a sensor element temperature, which is a temperature of the heater or the element body, reaches a predetermined target temperature,
    wherein after the heater control process is started, when the sensor element temperature reaches a level higher than or equal to a predetermined threshold lower than or equal to the target temperature, the pump cell controller starts the start-up time measurement pump control process.

3. The gas sensor according to claim 1,
    wherein the sensor element has an adjustment pump cell that adjusts an oxygen concentration in an oxygen concentration adjustment chamber provided on an upstream side of the measurement chamber of the measurement-object gas flow portion, and
    the pump cell controller executes an adjustment pump control process of operating the adjustment pump cell at the start-up time of the sensor element, and when determining based on the operation of the adjustment pump cell that the oxygen concentration in the oxygen concentration adjustment chamber is stabilized, makes switching from the start-up time measurement pump control process to the normal time measurement pump control process.

4. The gas sensor according to claim 3,
    wherein the oxygen concentration adjustment chamber has a first internal cavity, and a second internal cavity provided on a downstream side of the first internal cavity and on the upstream side of the measurement chamber,
    the adjustment pump cell has a main pump cell that adjusts an oxygen concentration in the first internal cavity, and an auxiliary pump cell that adjusts an oxygen concentration in the second internal cavity,
    the adjustment pump control process includes an auxiliary pump control process of controlling the auxiliary pump cell so that the oxygen concentration in the second internal cavity reaches a target concentration, and a main pump control process of controlling the main pump cell so that an auxiliary pump current which flows through the auxiliary pump cell by the auxiliary pump control process reaches a target current, and
    when determining that the auxiliary pump current is stabilized at around the target current, the pump cell controller makes switching from the start-up time measurement pump control process to the normal time measurement pump control process.

5. The gas sensor according to claim 1,
    wherein when an open time measurement voltage reaches a level higher than or equal to a predetermined threshold, the pump cell controller makes switching from the start-up time measurement pump control process to the normal time measurement pump control process, the open time measurement voltage being the measurement voltage in a state in which no control is performed to pass a current through the inner measurement electrode and the reference electrode.

6. The gas sensor according to claim 1,
    wherein the inner measurement electrode contains at least one of Pt and Rh.

7. The gas sensor according to claim 1,
wherein volume C of the inner measurement electrode is $8 \times 10^{-3}$ mm$^3$ or more and $32 \times 10^{-3}$ mm$^3$ or less, and
a difference $\Delta V$ between the start-up time target value and the normal time target value is 120 mV or more and 200 mV or less.

\* \* \* \* \*